United States Patent [19]
Walt et al.

[11] Patent Number: 5,320,814
[45] Date of Patent: * Jun. 14, 1994

[54] FIBER OPTIC ARRAY SENSORS, APPARATUS, AND METHODS FOR CONCURRENTLY VISUALIZING AND CHEMICALLY DETECTING MULTIPLE ANALYTES OF INTEREST IN A FLUID SAMPLE

[75] Inventors: David R. Walt, Lexington, Mass.; Steven M. Barnard, Basel, Switzerland

[73] Assignee: Trustees of Tufts College, Medford, Mass.

[*] Notice: The portion of the term of this patent subsequent to Sep. 14, 2010 has been disclaimed.

[21] Appl. No.: 981,884

[22] Filed: Nov. 25, 1992

Related U.S. Application Data

[63] Continuation-in-part of Ser. No. 645,787, Jan. 25, 1991, Pat. No. 5,244,636.

[51] Int. Cl.⁵ ............................................. G01N 21/00
[52] U.S. Cl. .............................. 422/82.07; 422/82.06; 436/172; 436/167; 128/643; 385/12
[58] Field of Search ............... 422/82.07, 82.06, 82.08, 422/82.09, 86, 88; 128/634; 385/12; 436/167, 172, 127, 128, 129, 130, 139, 140, 141, 142, 800; 250/227.23

[56] References Cited

U.S. PATENT DOCUMENTS

| | | | |
|---|---|---|---|
| 4,523,092 | 6/1985 | Nelson | 250/227.23 |
| 4,582,809 | 4/1986 | Block et al. | 422/82.08 |
| 4,785,814 | 11/1988 | Kane | 128/634 |
| 4,822,746 | 4/1989 | Walt | 436/172 |
| 4,999,306 | 3/1991 | Yafuso et al. | 422/82.07 |
| 5,019,350 | 5/1991 | Rhum et al. | 422/82.08 |
| 5,047,627 | 9/1991 | Yim et al. | 128/634 |

FOREIGN PATENT DOCUMENTS

0336985 10/1989 European Pat. Off. ............ 128/634

*Primary Examiner*—Robert J. Warden
*Assistant Examiner*—T. A. Trembley
*Attorney, Agent, or Firm*—David Prashker

[57] ABSTRACT

The present invention provides a unique fiber optic sensor which is able to provide a viewing zone for visual examination of a sample and its surrounding environment; and is able to conduct multiple assays concurrently using a plurality of different dyes immobilized at individual spatial positions within a dye sensing zone on the surface of the sensor. The present invention also provides apparatus for making precise optical determinations and measurements for multiple analytes of interest concurrently and provides methods of detection for multiple analytes of interest which can be correlated with specific parameters or other ligands for specific applications and purposes.

12 Claims, 24 Drawing Sheets

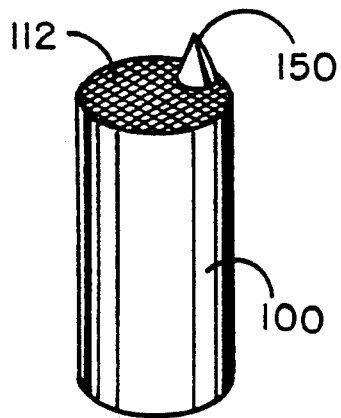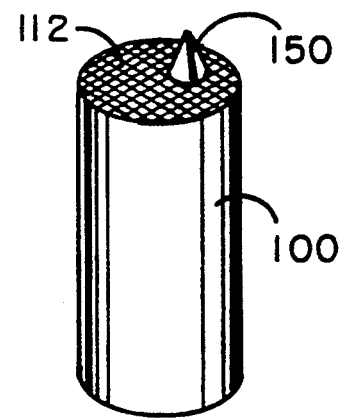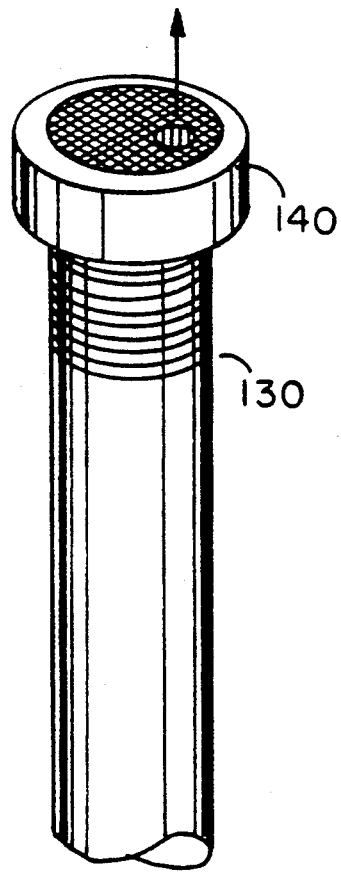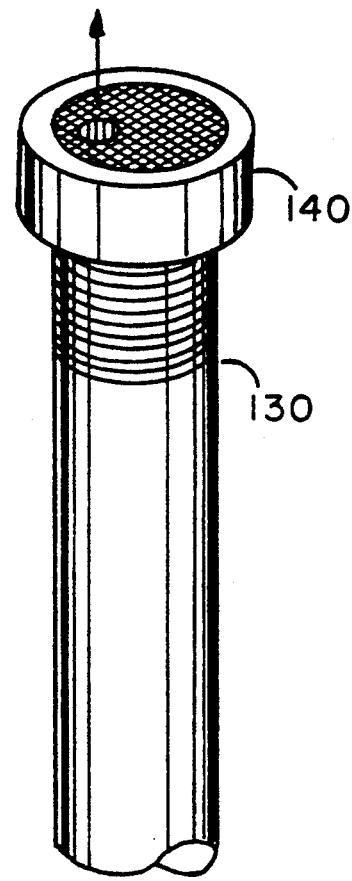
FIG. 10　　　　　　　　FIG. 11

FIBER OPTIC ARRAY SENSORS, APPARATUS, AND METHODS FOR CONCURRENTLY VISUALIZING AND CHEMICALLY DETECTING MULTIPLE ANALYTES OF INTEREST IN A FLUID SAMPLE

CROSS-REFERENCE

This application is a Continuation-In-Part of U.S. patent application Ser. No. 645,787 Filed Jan. 25, 1991, now U.S. Pat. No. 5,244,636.

FIELD OF THE INVENTION

The present application is generally concerned with fiber optic sensors and light absorbing dyes which in combination are employed for qualitative and quantitative analytical determinations; and is specifically directed to the preparation and use of a single fiber optic array as a sensor for the detection of multiple analytes of interest concurrently.

BACKGROUND OF THE INVENTION

The use of optical fibers and optical fiber strands in combination with light energy absorbing dyes for medical, biochemical, and chemical analytical determinations has undergone rapid development, particularly within the last decade The use of optical fibers for such purposes and techniques is described by Milanovich et al, "Novel Optical Fiber Techniques for Medical Application", Proceedings of the SPIE 28th Annual International Technical Symposium on Optics and Electro-Optics, Volume 494, 1980; Seitz, W. R., "Chemical Sensors Based on Immobilized Indicators and Fiber Optics" in *C.R.C. Critical Reviews In Analytical Chemistry*, Vol. 19, 1988, pp. 135-173; Wolfbeis, O. S., "Fiber Optical Fluorosensors In Analytical Chemistry" in *Molecular Luminescence Scectroscopy, Methods and Applications* (S. G. Schulman, editor), Wiley & Sons, New York; Angel, S. M., Spectroscopy 2(4): 38 (1987); and Walt et al., "Chemical Sensors and Microinstrumentation", ACS Symposium Series, Volume 403, 1989, p. 252. The optical fiber strands typically are glass or plastic extended rods having a small cross-sectional diameter. When light energy is projected into one end of the fiber strand (conventionally termed the "proximal end"), the angles at which the various light energy rays strike the surface are greater than the critical angle; and such rays are "piped" through the strand's length by successive internal reflections and eventually emerge from the opposite end of the strand (conventionally termed the "distal end"). Typically bundles of these strands are used collectively as optical fibers in a variety of different applications.

For making an optical fiber into a sensor, one or more light energy absorbing dyes are attached to the distal end of the optical fiber. The sensor can then be used for both in-vitro and/or in-vivo applications. As used herein, light energy is photoenergy and is defined as electromagnetic radiation of any wavelength. Accordingly, terms "light energy" and "photoenergy" include infrared, visible, and ultraviolet wavelengths conventionally employed in most optical instruments and apparatus; the term also includes the other spectral regions of x-ray and microwave wavelengths (although these are generally not used in conjunction with optical fibers).

Typically, light from an appropriate energy source is used to illuminate what is chosen to be the proximal end of an optical fiber on a fiber bundle. The light propagates along the length of the optical fiber; and a portion of this propagated light energy exits the distal end of the optical fiber and is absorbed by one or more light energy absorbing dyes. The light energy absorbing dye may or may not be immobilized; may or may not be directly attached to the optical fiber itself; may or may not be suspended in a fluid sample containing one or more analytes of interest to be detected; and may or may not be retainable for subsequent use in a second optical determination.

Once the light energy has been absorbed by the dye, some light energy of varying wavelength and intensity returns through the distal end of the optical fiber and is conveyed through either the same fiber or a collection fiber or fibers to a detection system where the emerging light energy is observed and measured. The interactions between the light energy conveyed by the optical fiber and the properties of the light absorbing dye—in the presence of a fluid sample containing one or more analytes of interest and in the absence of any analytes whatsoever—provide an optical basis for both qualitative and quantitative determinations. Merely illustrating the use of optical fiber sensors presently known in a variety of conditions, apparatus, dyes and applications are U.S. Pat. Nos. 4,822,746; 4,144,452; 4,495,293; and Re. 31,879.

Most light detection systems employ a photo sensitive detector such as a photodiode or photomultiplier tube. Spatial resolution of light is possible with two dimensional detectors such as video, cameras, and charge coupled devices. Moreover, in view of the microcircuitry and enhanced television technology presently available, a variety of light image processing and analytical systems have come into existence in order to both enhance, analyze and mathematically process the light energies introduced to and emerging from the absorbing dyes in such optical analytical techniques. Typically, these systems provide components for photon measurement and include image capture; data acquisitions; data processing and analysis; and visual presentation to the user. Commercially available systems include the QX-7 image processing and analysis system sold by Quantex, Inc. (Sunnydale, Calif.); and the IM Spectrofluorescence imaging system offered by SPEX Industries, Inc. (Edison, N.J.). Each of these systems may be combined with microscopes, cameras, and/or television monitors for automatic processing of all light energy determinations.

Of the many different classes of light absorbing dyes which conventionally are employed with bundles of fiber strands and optical fibers for different analytical purposes are those compositions which emit light energy after absorption, termed "fluorophores"; and those which absorb light energy and internally convert the absorbed light energy rather than emit it as light, termed "chromophores."Fluorophores and fluorescent detection methods employing optical fibers are recognized as being markedly different and distinguishable from light energy absorbance and absorption spectroscopy.

Fluorescence is a physical phenomenon based upon the ability of some molecules to absorb light energy (photons) at specified wavelengths and then emit light energy of a longer wavelength and at a lower energy. Such emissions are called fluorescence if the emission is relatively long-lived, typically $10^{-11}$ to $10^{-7}$ seconds.

Substances able to fluoresce share and display a number of common characteristics: the ability to absorb light energy at one wavelength or frequency; reach an excited energy state; and subsequently emit light at another light frequency and energy level. The absorption and fluorescence emission spectra are thus individual for each fluorophore; and are often graphically represented as two separate curves which are slightly overlapping. All fluorophores demonstrate the Stokes' Shift—that is, the emitted light is always at a longer wavelength (and at a lower energy level) relative to the wavelength (and energy level) of the excited light absorbed by the substance. Moreover, the same fluorescence emission spectrum is generally observed irrespective of the wavelength of the exciting light and, accordingly, the wavelength and energy of the exciting light may be varied within limits; but the light emitted by the fluorophore will always provide the same emission spectrum as emerging light of a different wavelength although it may have an altered intensity. Finally, fluorescence may be measured as the quantum yield of light emitted. The fluorescence quantum yield is the ratio of the number of photons emitted in comparison to the number of photons initially absorbed by the fluorophore. For more detailed information regarding each of these characteristics the following references are recommended: Lakowicz, J. R., *Principles of Fluorescence Spectroscopy*, Plenum Press, New York 1983; Freifelder, D., Physical Biochemistry, second edition, W. H. Freeman and Company, New York, 1982; "Molecular Luminescence Spectroscopy Methods and Applications: Part I" (S. G. Schulman, editor) in *Chemical Analysis*, Vol. 77, Wiley & Sons, Inc., 1985; The *Theory of Luminescence*, Stepanov and Gribkovskii, Iliffe Books, Ltd, London, 1968.

In comparison, substances which absorb light energy and do not fluoresce usually convert the light energy into heat or kinetic energy. The ability to internally convert the absorbed light energy identifies the dye as a "chromophore." Dyes which absorb light energy as chromophores do so at individual wavelengths of energy and are characterized by a distinctive molar absorption coefficient at that wavelength. Chemical analyses employing fiber optic strands and absorption spectroscopy using visible and ultraviolet light wavelengths in combination with the absorption coefficient allow for the determination of concentration for specific analytes of interest by spectral measurement. The most common use of absorbance measurement via optical fibers is to determine concentration, which is calculated in accordance with Beers' law; accordingly, at a single absorbance wavelength, the greater the quantity of the composition which absorbs light energy at a given photo wavelength, the greater the optical density for the sample. In this way, the total quantity of light absorbed directly correlates with the quantity of the composition in the sample.

Many of the recent improvements employing optical fiber sensors in both qualitative and quantitative analytical determinations concern the desirability of depositing and/or immobilizing various light absorbing dyes at the distal end of the optical fiber using a given technique or apparatus. In this manner, a variety of different optical fiber chemical sensors and methods have been reported for specific analytical determinations and applications such as pH measurement, oxygen detection, and carbon dioxide analyses. These developments are exemplified by the following publications: Freeman et al., *Anal. Chem.* 53:98 (1983); Lippitsch et al., *Anal. Chem. Acta.* 205:1, (1988); Wolfbeis et al., *Anal. Chem.* 60:2028 (1988); Jordan et al., *Anal. Chem.* 59:437 (1987) Lubbers et al., Sens. Actuators 1983; Munkholm et al, Talanta 35:109 (1988); Munkholm et al., *Anal. Chem.* 581427 (1986); Seitz, W. R. *Anal. Chem.* 56:16A–34A (1984); Peterson et al., *Anal. Chem.* 52:864 (1980): Saari et al., Anal. Chem. 54:821 (1982); Saari et al. Anal. Chem. 55:667 (1983); Zhujun et al., Anal. Chem. 56:2199 (1984).

Despite these many innovations and developments, and without regard to whether the application is intended for in-vitro or in-vivo use, it was previously and remains today nearly impossible to measure multiple parameters and detect multiple analytes of interest in a fluid sample using a single optical fiber sensor. The axiomatic rule almost universally accepted is: one dye allows but one optical determination. Presently therefore, a single fiber optical sensor can measure but one individual chemical analyte or species in a fluid sample. If more than one analytical determination is required, the use of several different fiber optical sensors each having a different single dye reagent are needed.

It is most important to recognize and to understand the reasons and basis for the axiomatic rules' existence and acceptance. The useful spectral range for optical fibers is approximately 300–700 nm, a range due principally to higher attentuation outside this wavelength region. Most dyes have relatively broad excitation (absorption) and/or emission spectra Consequently, when two or more dyes are combined (each dye being sensitive to a different analyte), there is typically significant overlap in their spectra; and this spectral overlap results in difficult-to-deconvolute signals arising from the returning (emerging) light from each dye. It is important to note that the optical fibers conventionally used for fiber optic sensors randomly mix all the light energy returning (emerging) from the distal end of the sensor. Thus, even if the dyes were positioned differently on the distal end of the sensor, the returning signals (emerging light energy) would still become randomly scrambled and therefore be rendered useless for making optical determinations. Only a very few sensor systems have been developed in which the sensor utilizes a plurality of dyes with minimal spectral overlap. Thus for general use purposes, the axiomatic rule has evolved that one dye permits but one optical determination.

Given the very few exceptions to the axiomatic rule, all conventional optical fiber sensors and systems now available demand the presence of a separate sensing optical fiber and dye reagent for each parameter or analyte to be measured. Each sensing fiber increases the size and complexity of the overall system; and geometrically increases the complexity and difficulty of making multiple optical determinations concurrently. Accordingly, the development of a single imaging fiber optical sensor able to utilize multiple dye reagents and to provide multiple optical determinations of different analytes of interest concurrently would be recognized as a major advance and substantial improvement by persons ordinary skilled in this art.

SUMMARY OF THE INVENTION

The present invention is definable in alternative formats. A first definition provides a fiber optic sensor useful in an apparatus for detecting at least one analyte of interest in a fluid sample, the detection of each analyte of interest being correlatable with an individual optical determination, said fiber optic sensor comprising: a preformed, unitary fiber optic array comprising a plurality of individually clad, fiber optical strands disposed co-axially along their lengths and having two discrete optic array ends each of which is formed of multiple strand end faces said preformed, unitary fiber optic array being of determinable configuration and dimensions, said two discrete ends of said preformed unitary fiber optic array presenting two discrete optic array surfaces for introduction and conveyance of light energy;

at least one sensing zone comprising not less than one light energy absorbing dye disposed as an uninterrupted deposit in aligned organization upon multiple strand end faces on one of said discrete optic array surfaces of said preformed, unitary fiber optic array, the different spatial positioning of each dye deposit in aligned organization within said sensing zone on said discrete optic array surface serving to identify and distinguish each light energy absorbing dye from all other light energy absorbing dyes disposed within said dye sensing zone each spatially positioned dye reacting with one analyte of interest; and at least one sample viewing zone adjacent to said dye sensing zone on said discrete optic array surface of said preformed, unitary fiber optic array, said sample viewing zone being formed of multiple strand end faces in aligned organization and in fixed spatial position on said discrete optic array surface.

A second alternative definition of the present invention provides an apparatus for detecting at least one analyte of interest in a fluid sample, the detection of each analyte of interest being correlatable with an individual optical determination, said apparatus comprising:

a fiber optic sensor comprised of
(a) a preformed, unitary fiber optic array comprising a plurality of individually clad, fiber optical strands disposed co-axially along their lengths and having two discrete optic array ends each of which is formed of multiple strand end faces, said preformed, unitary fiber optic array being of determinable configuration and dimensions, said two discrete ends of said unitary fiber optic array presenting two discrete optic array surfaces for introduction and conveyance of light energy,
(b) at least one sensing zone comprising not less than one energy absorbing dye disposed as an uninterrupted deposit in aligned organization upon multiple strand end faces on one of said discrete optic array surfaces of said preformed, unitary fiber optic array, the different spatial positioning of each dye deposit in aligned organization within said sensing zone on said discrete optic array surface serving to identify and distinguish each light energy absorbing dye from all other light energy absorbing dyes disposed within said dye sensing zone, each spatially positioned dye reacting with one analyte of interest, and
(c) at least one sample viewing zone adjacent to said sensing zone on said discrete optic array surface of said preformed, unitary optic array, said sample viewing zone being formed of multiple strand end faces in aligned organization and in fixed spatial position on said discrete optic array end;

means for placing said spatially positioned dye within said sensing zone on said optic array surface of said fiber optic sensor into reactive contact with a fluid sample;

means for introducing light energy to an optic array surface of said fiber optic sensor such that said fiber optical strands convey said introduced light energy concurrently and illuminate said spatially positioned dye within said sensing zone on said optic array surface;

means for detecting emerging light energy from said illuminated spatially positioned dye within said sensing zone on said optic array surface, said detected emerging light energy serving as an optical determination for one analyte of interest in the fluid sample; and means for concurrently observing the fluid sample via said sample viewing zone on said optic array surface.

A third alternative definition provides a method for detecting at least one analyte of interest in a fluid sample, the detection of each analyte of interest being correlatable with an individual optical determination, said method comprising the steps of: obtaining a fiber optic sensor comprised of a preformed, unitary fiber optic array comprising a plurality of individually clad, fiber optical strands disposed co-axially along their lengths and having two discrete optic array ends each of which is formed of multiple strand end faces, said preformed, unitary fiber optic array presenting two discrete optic array surfaces for introduction and conveyance of light energy, at least one sensing zone comprising not less than one energy absorbing dye disposed as an uninterrupted deposit in aligned organization upon multiple strand end faces on one of said discrete optic array surfaces of said preformed, unitary fiber optic array, the different spatial positioning of each dye deposit in aligned organization upon said discrete optic array surface serving to identify and distinguish each light energy absorbing dye from all other light energy absorbing dyes which may be disposed within said sensing zone, each spatially positioned dye reacting with one analyte of interest, and at least one sample viewing zone adjacent to said sensing zone on said discrete optic array surface on said preformed, unitary fiber optic array, said sample viewing zone being formed of multiple strand end faces in aligned organization and in fixed spatial position on said discrete optic array surface;

placing said spatially positioned dye within said sensing zone on said optic array surface of said fiber optic sensor into reactive contact with a fluid sample;

introducing light energy to an optic array surface of said fiber optic sensor such that said fiber optical strands convey said introduced light energy concurrently and illuminate said spatially positioned dye within said sensing zone on said optic array surface;

detecting emerging light energy from said illuminated spatially positioned dye within said dye sensing zone on said optic array surface, said detected emerging light energy serving as an optical determination for one analyte of interest in the fluid sample; and concurrently observing the fluid sample via said sample viewing zone on said optic array surface.

BRIEF DESCRIPTION OF THE FIGURES

The present invention may be more easily and completely understood when taken in conjunction with the accompanying drawing, in which:

FIGS. 8–13 illustrate the manipulative steps performed during the deposition of photopolymerized dyes individually at precise spatial positions within a dye sensing zone on the distal optic array surface of FIG. 6;

DETAILED DESCRIPTION OF THE INVENTION

Figure 1:
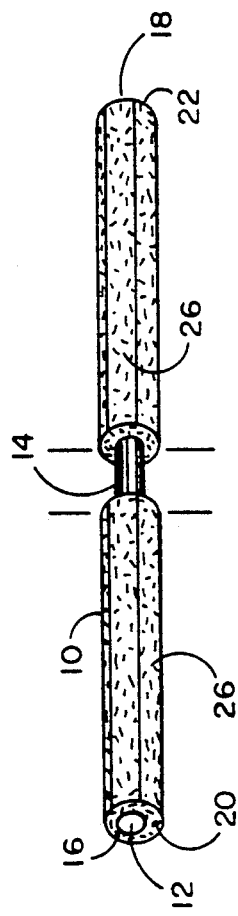
FIG. 1 is an overhead view of a preferred, individually clad, fiber optical strand.

The present invention is a marked improvement in fiber optic sensors; apparatus, systems and assemblies; and methods for performing qualitative and quantitative optical measurements using a unique fiber optic sensor. The physical construction of this singular fiber optic sensor and the manner of its making are the critical and demanding aspects of the invention. The apparatus, methods for making determinations, and systems of qualitative and quantitative detection subsequently described are based and rely upon the existence and use of the unique fiber optic sensor as an essential component.

Although the unique fiber optic sensor and the other aspects of the present invention may bear a superficial similarity to conventionally known optical fibers, fiber optic strands, and fluorometric and colorimetric optical systems for making analytical determinations, it will be recognized and appreciated that the present invention provides multiple benefits and major advantages not previously available heretofore. These include:

1. A fully constructed fiber optical sensor comprising a preformed, unitary fiber optic array composed of individually clad, fiber optical strands disposed co-axially along their lengths and which has at least two uninterrupted light energy absorbing dye deposits disposed individually at different spatial positions upon one end surface of the optic array. This unique fiber optic sensor permits the use of one or more chemical sensing dyes to measure a variety of different parameters such as pH, oxygen, carbon dioxide and the like using but a single discrete sensor. The use of multiple dyes in combination with a single, discrete imaging fiber optic array, in so far as is presently known, has never before been constructed for any purpose or application.

2. A variety of different in-vitro measurements and analytical determinations may now be made using a single fiber optic sensor prepared in accordance with the present invention. The in-vitro applications and assay techniques may be performed concurrently using one or multiple fluid samples. Each concurrently conducted measurement or determination for different analytes of interest is made individually, accurately, and precisely. The observed empirical results are then correlated and/or computed individually to provide precise information regarding a variety of different parameters or ligands individually.

3. The unique fiber optic sensor as well as the apparatus and measurement procedures described hereinafter may be employed in a variety of different in-vivo conditions with both humans and animals. The present invention provides accurate and precise measurements and determinations using a single discrete fiber optic sensor rather than the conventional bundle of different sensors joined together for limited purposes. The present invention thus provides a minimum-sized diameter sensor for in-vivo catherization; a minimum intrusion into the bloodstream or tissues of the living subject for assay purposes; and a minimum of discomfort and pain to the living subject coupled with a maximum of accuracy and precision as well as multiplicity of parameter measurement in both qualitative and/or quantitative terms.

4. The present invention provides a fiber optic sensor suitable for use with multiple light systems and apparatus; and is particularly suitable for use with two or more light energy absorbing dye compositions having overlapping spectral properties. Unlike conventionally known fiber optic systems which are typically limited to certain light energy ranges or wavelengths exclusively, the present invention may be prepared and employed with any measurable range of light energy or wavelength which can be conveyed or propagated through a fiber optic strand including infrared light, visible light and ultraviolet light wavelengths. The diversity and range of the sensor is limited only by the choice of light energy absorbing dye available from the entirety of those conventionally known today.

5. The fiber optic sensors of the present invention permit the use of light-absorbing dyes for making different analytical determinations and measuring multiple parameters concurrent with visual inspection of the sample. Clearly, via the requirement of fixed spatial positions for the dye within a dye sensing zone on the optic array end surface, a spatial resolution of the forthcoming individual light energy intensities and wavelengths is created. Moreover, an effective separation of individual light signals is made and a concomitant avoidance of photon intermixing is maintained. There is, therefore, no overlap of spectral properties and characteristics between the different spatial locations with the dye sensing zone despite the use of a single dye. Similarly, there is no need for spectral resolution of the different light energy signals emanating from the dye sensing zone because of the spatial resolution effects caused by the individual spatial positionings for the single dye. Accordingly, the user can observe the contents of the sample via the viewing zone at any time during, before, or after performing the chemical analyses with the dye.

6. The present invention optionally permits the user to employ the unique fiber optic sensor in a fully automated, monitored, and even computerized system. A number of alternative apparatus formats are possible and suitable. The goal of all these automated systems is to provide the user with an apparatus that can display light intensity and location nearly simultaneously. Typically, they are of two general types: phototubes and charge coupled devices (or "CCD's"). A conventional constructed camera is but one example of such automated apparatus; and in an extreme case, even the detection elements in the camera could be used alone.

In one desirable apparatus format, the unique optic fiber sensor is employed with a microscope objective, a camera, a visual monitor, and a computerized image processing and analytical program. In this embodiment providing a fully automated, computer-controlled processing apparatus and measurement system, the intensity and wavelength of light energy is carefully controlled; the light energy is introduced to the fiber optic sensor at specifically controlled occasions and durations; and the resulting optic images and emerging light photons conveyed for visualization and/or analytical measurement are mathematically processed and correlated via computer programs into immediately useful data and often visualized on a television monitor or other display apparatus by using such fully automated, computerized apparatus and analytical systems. Not only are a variety of different optical determinations made and diverse parameters measured concurrently within a single fluid sample; but also many different fluid samples may be observed and analyzed individually seratim for detection of multiple analytes of interest or visual imaging concurrently—each individual fluid sample following its predecessor in series.

7. The singular fiber optic sensor of the present invention allows the user to conduct both chemical analyses and optical viewing by employing but one construction system. The sensor, being comprised of fiber optical strands, permits direct chemical analyses and on-demand viewing of the sample environment in which the sensor is placed. The analytic determinations involving the immobilized dyes of the sensor and the assessment of various parameters may be performed at will as the needs or desires of the user requires. The dual capability of direct viewing and chemical analysis using a single sensor is particularly advantageous for in-vivo applications such as angioplasty where it would be most desirable to see where the optical fiber lies within the patient; use the fiber to deliver the therapeutic treatment (such as a laser light treatment); as well as to concurrently measure the efficacy of the treatment (such as cholesterol or calcium ion values immediately after laser light treatment).

Since the present invention is definable in multiple formats and may be employed in different modes for a variety of divergent purposes and applications, the subject matter as a whole which is the present invention will be presented and described individually as component parts and then collectively as assemblies in order that the prospective user may more quickly recognize and appreciate their major differences and distinctions in comparison to the fiber optic apparatus and systems conventionally known.

I. The Organization and Construction of the Singular Fiber Optic Sensor

The unique fiber optic sensor comprises three essential components: a preformed, unitary fiber optic array comprised of a plurality of individually clad fiber optical strands disposed co-axially along their lengths; one or more light energy absorbing dyes disposed individually within dye sensing zone; and a sample viewing zone. Each component will be described in detail.

A. The Preformed, Unitary Fiber Optic Array

The unique fiber optic array, its organization and construction, and its component parts are illustrated by FIGS. 1-8 respectively. Each discrete, unitary fiber optic array is a preformed bundle comprised of a plurality of individually clad, fiber optical strands disposed coaxially along their lengths. The smallest common repeating unit within the preformed array is thus a single fiber optical strand. The manner in which these optical fiber strands are prepared and the manner in which these prepared optical strands are joined collectively into an organized optic array are conventionally known, but are fundamental to a proper understanding and use of the present invention.

The individually clad, optical fiber strand

Figure 2A:
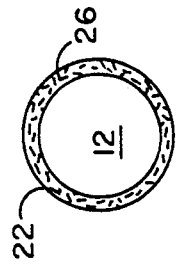
FIGS. 2A and 2B are views of the proximal and distal surfaces of the fiber optical strand of FIG. 1.
Figure 2B:

A preferred optical fiber strand is illustrated by FIGS. 1 and 2A and 2B. As seen therein, an individual optical fiber strand 10 is comprised of a single optical fiber 12 having a rod-like shaft 14 and two fiber ends 16, 18, each of which provides a substantially planar end surface. The intended distal surface 20 at the fiber end 16 is illustrated by FIG. 2A while the intended proximal surface 22 at the fiber end 18 is illustrated within FIG. 2B. It will be recognized and appreciated that the terms "proximal" and "distal" are relative and interchangeable until the strand is ultimately positioned in an apparatus. The optical fiber 12 is composed typically of glass or plastic and is a flexible rod able to convey light energy introduced at either of its ends 16 and 18. Such optical fibers 12 are conventionally known and commercially available. Alternatively, the user may himself prepare individual optical fibers in accordance with the practices and techniques reported in the scientific and industrial literature. Accordingly, the optical fiber 12 is deemed to be conventionally known and available as such.

It will be appreciated that FIGS. 1-2 are illustrations in which the features have been purposely magnified and exaggerated beyond their normal scale in order to provide both clarity and extreme detail. Typically, the conventional optical fiber has a cross section diameter of 5-500 micrometers; and is routinely employed in lengths ranging between meters (in the laboratory) to kilometers (in field telecommunications). Moreover, although the optical fiber 12 is illustrated via FIGS. 1-2 as a cylindrical extended rod having substantially circular proximal and distal end surfaces, there is no requirement or demand that this specific configuration be maintained. To the contrary, the optical fiber may be polygonal or asymmetrically shaped along its length; provided special patterns and shapes at the proximal and/or distal faces; and need not present an end surface which is substantially planar. Nevertheless, for best efforts, it is presently believed that the substantially cylindrical rod-like optical fiber having planar and surfaces is most desirable.

Each optical fiber 12 is desirably, but not necessarily individually clad axially along its length by cladding 26. This cladding 26 is composed of any material with a lower refractive index than the core and prevents the transmission of light energy photons from the optical fiber 12 to the external environment. The cladding material 26 may thus be composed of a variety of radically different chemical formulations including various glasses, silicones, plastics, cloths, platings, and shielding matter of diverse chemical composition and formulation. The manner in which the optical fiber 12 is clad is also inconsequential and of, no import to the present invention. Those methods of deposition, extrusion, and covering are scientifically and industrially available; and any of these known processes may be chosen to meet the requirements and convenience of the user. Moreover, the quantity of cladding employed need be energy conveyed by the optical fiber 12 from escaping into the ambient environment. It will be recognized and appreciated therefore, that the depth of cladding 26 as appears within FIGS. 1 and 2 respectively is greatly exaggerated and purposely thickened in appearance in order to show the general relationship; and is without scale or precise ratios between the cladding 26 and the optical fiber 12.

It will also be recognized that the configuration of the cladding 26 as shown by FIGS. 1 and 2 has been shaped as a circular coating as a preferred embodiment only. For reasons as will become clear subsequently, it is desirable that the cladding 26 take form in regular geometric form as a round circular shape. The illustrated configuration, however, is merely a preferred embodiment of the cladding 26 as it extends co-axially along the length of the optical fiber 12. For purposes of added clarity also, FIG. 1 reveals the individually clad, optical fiber strand 10 in partial cross-section to demonstrate the relationship between the optical fiber 12 and the cladding 26 which is coextensive along its length.

Figure 3A:
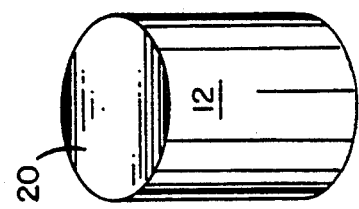
FIGS. 3A and 3B are alternative constructions of the optical end surface for the fiber optical strand of FIG. 1.
Figure 3B:
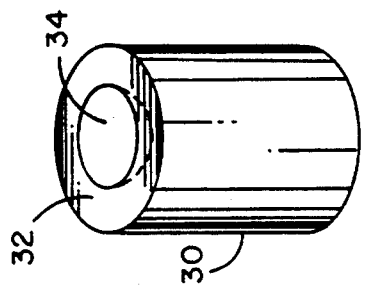

The user also has a variety of choices at his discretion regarding the configuration of the "distal" end 16 of the optical fiber 12 as is shown by FIGS. 3A and 3B. As seen in FIG. 3A, the "distal" end 16 is substantially cylindrical in shape and desirably presents a surface 20 which is substantially planar and smooth. As an alternative in FIG. 3B, the distal end 30, while maintaining its substantially cylindrical shape, nevertheless provides a very different end surface for the optical fiber 12. The surface 32 includes a depression or well 34 which extends into the substance of the optical fiber 12 at a depth typically of several micrometers. Although the well 34 appears substantially circular within FIG. 3B, oval or irregularly configured depressions may also be employed as fits the needs or convenience of the user. Similarly, the void volume of the well 34 from its greatest depth to the proximal surface 32 may also be considerably varied.

It will be recognized and appreciated as well that the range and variety of dimensional and configurational divergence for the strand end is limited only by the user's ability to subsequently dispose and immobilize a dye composition/formulation on the intended distal surface of the optical fiber 12. The alternative illustrated by FIG. 3B will increase the quantity of dye materials deposited and also permit a greater surface area of dye for reactive contact on the surface for specific uses and assay applications. In some embodiments, the greatest possible surface area configurations of the distal end surface may be highly desirable as an aid; nevertheless, for most general assay purposes, both quantitative and qualitative, the intended distal surface illustrated within FIG. 3A as a substantially planar and smooth surface is deemed to be suitable and desirable.

For general construction of the fiber optic sensor and for most purposes and applications of the improved optical detecting system and procedures described hereinafter, it is desirable to employ the individually clad, fiber optical strand illustrated by FIGS. 1, 2A, 2B in preference to a bare, unsheathed strand. Clearly, the optical fiber strand 10 of FIG. 1 comprising a single optical fiber is unable to transmit light energy photons to any other optical fiber or strand due to the cladding material 26 which forms a sheath. This sheath, having a refractive index less than the strand core, prevents loss of light energy photons into the general environment. Accordingly, the potential for photon loss, distortion, or other optical error is minimized and reduced. For these reasons, the individually clad optical fiber mode of construction is preferable to the use of bare optical fiber strands in order to achieve greater precision and accuracy.

The preformed, unitary array

While the single repeating unit comprising the preformed fiber optic sensor is the individually clad, fiber optic strand described previously, it is the organizational positioning and alignment of the many individually clad, fiber optical strands as a unitary array which is an essential component of the invention. A typical coherent fiber optic array is illustrated by FIGS. 4-6 respectively.

Figure 4:
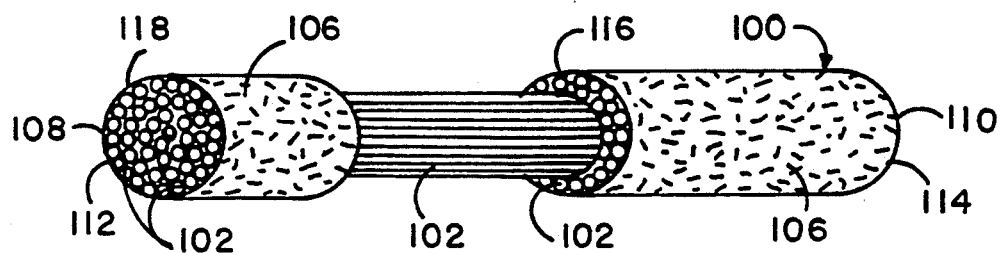
FIG. 4 is an overhead view of a preformed, unitary fiber optical array using the fiber optic strand of FIG. 1.

The unitary fiber optical array 100 appears in exaggerated, highly simplified views without regard to scale within FIG. 4. The preformed array is composed of a plurality of individually clad, fiber optical strands which collectively lie co-axially along their respective lengths as the discrete, unitary optic array 104 of fixed and determinable configuration and dimensions. The optic array 104 has a unitary, rod-like collective body 106 and intended distal and proximal collective ends 108, 110 formed of multiple strand end faces. The intended distal collective end 108 provides a substantially planar and smooth optic array surface 112; similarly, the intended proximal collective end 110 provides a optic array surface 114. The topographical surface 116 is the result of the cladding of each fiber optical strand 102 collectively with such additional coating material 118 such that the many strands remain together collectively as a discrete and unitary whole. In this manner, the exterior surface 116 of the collective array body 106 may be configured and dimensioned as an assembly in an acceptable manner and useful manner. It will be recognized and appreciated also that a substantially cylindrical configuration and topography is maintained and presented by the unitary imaging fiber optic array 100 merely as one preferred embodiment. Any other regular or irregular configuration and design may be achieved and employed to satisfy the individual user's needs or desires.

Figure 5:
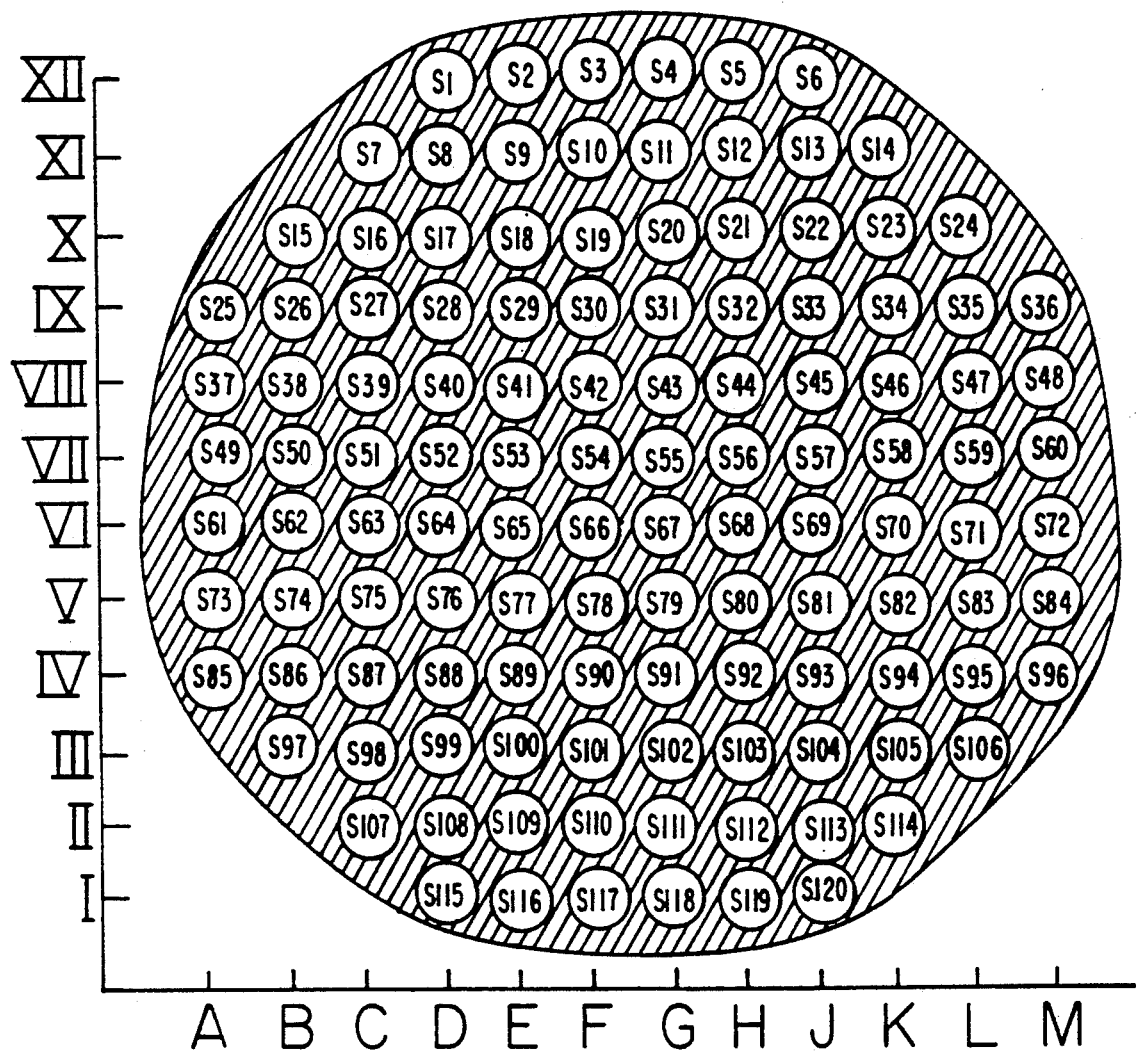
FIG. 5 is a view of the intended distal optical array surface of the unitary fiber optic array of FIG. 4.
Figure 6:
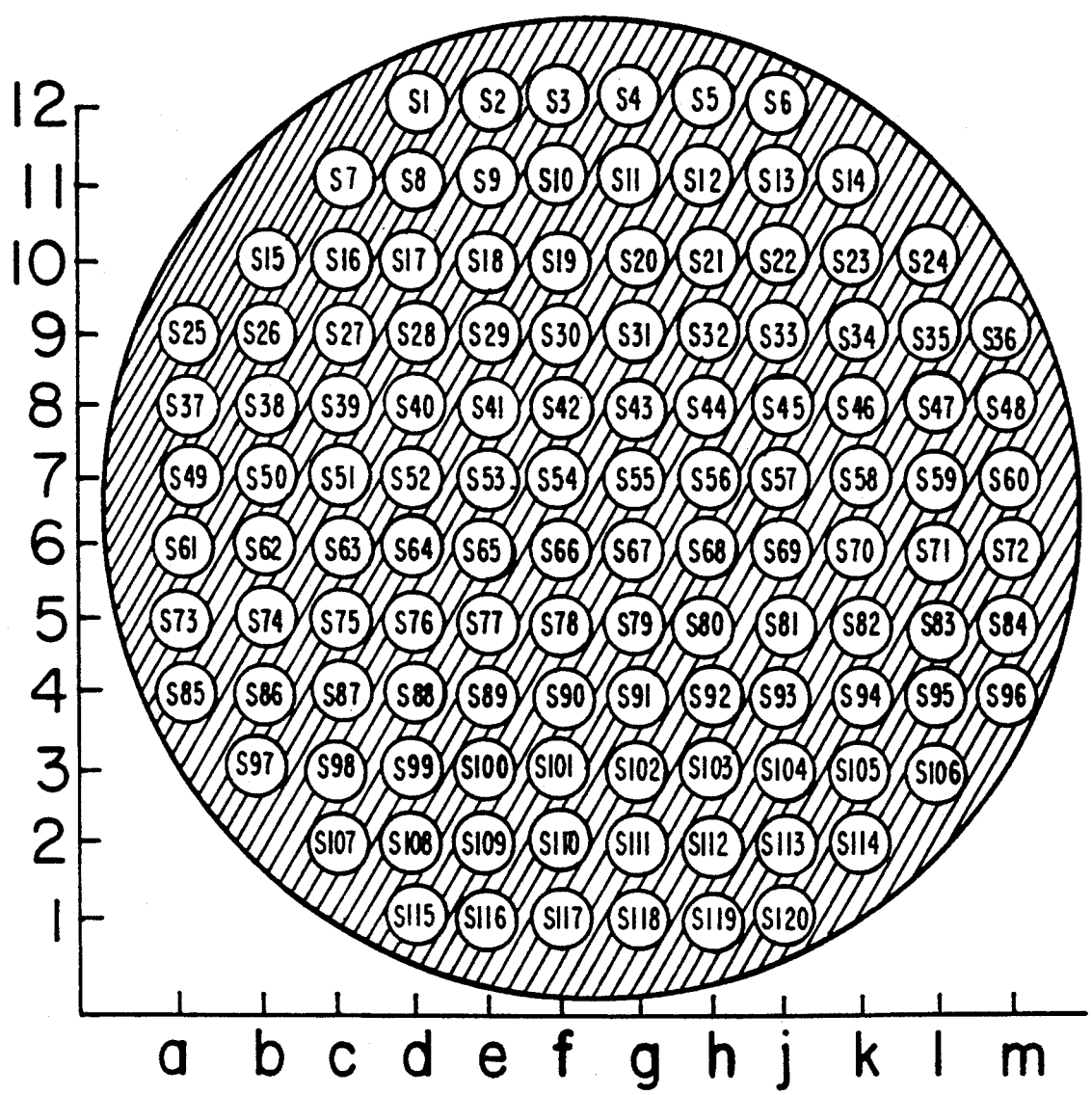
FIG. 6 is a view of the intended proximal optical array surface of the unitary fiber optic array of FIG. 4.

For purposes of clarity and ease of understanding, FIGS. 5 and 6 present a very limited and greatly reduced number of individually clad, fiber optical strands 102 present within the preformed optical array 104. A total of only 120 individually clad, fiber optical strands are seen to comprise the optical array 104 in greatly magnified and scale exaggerated views. Moreover, the relationship of the optical array surface 112 (the intended distal end) with respect to the other optical array surface 114 (the intended proximal end) becomes simplified and more-readily appreciated when using this limited number of 120 optical fiber strands. In practice and reality, however, it is estimated that there typically are 1000-3000 optical fiber strands in a conventional array of 0.5 mm diameter; and, up to 10,000 strands can be aligned in a 300 μm diameter distance. Thus the true total number of individually clad, fiber optic strands forming the unitary imaging fiber optic array will be almost as great, the total number varying with the cross-sectional diameter of each optical fiber and the thickness of the cladding material employed when constructing the optical fiber strands themselves.

The construction, organization, and positional alignment within a typical fiber optical unitary array is revealed by FIGS. 4–6. For descriptive purposes only, each of the individually clad, optical fiber strands is presumed to be linearly straight in position and has been arbitrarily assigned an identifying number S1–S120 as shown via FIGS. 5 and 6. The intended distal optic array surface 112 of FIG. 5 shows that each of the individual fiber optical strands S1–S120 can be identified and distinguished from its adjacently disposed neighbor as well as from any other optical fiber strand within the preformed array 104 by a set of spatial positioning coordinate numbers for the strand end faces. The intended distal optic array surface 112 may thus be arbitrarily divided into two axial directions as is illustrated by FIG. 5. The exact location of the S1 strand is thus identifiable by the numerical coordinates "XII D" showing the strand end face. Similarly, the exact spatial positioning and strand end face of the S72 fiber is designatable as "VIM". In this manner, the individual spatial position and strand end faces for each optical fiber strand S1–S120 is thus completely locatable and identifiable using the coordinate numeral labeling system.

The other optic array surface 114 (the intended proximal surface) allows for a similar mode of identification (presuming straight linear alignment of strands) by spatial positioning of each individual optical strand—again as a result of dual-axis numerical coordinates as seen in FIG. 6. Accordingly, fiber and strand end face S1 is located at numerical position "12$d$", and fiber S72 is identifiable, locatable, and distinguishable from all other fibers at the optic array surface by its individual numerical coordinates "6$m$". In this manner, the precise and exact position of each individually clad optical fiber strand and strand end faces on each of the discrete optic array surfaces 112, 114 can be located, identified, and specified via a series of two different numerical coordinates. The intended distal and proximal optic array surfaces are thus completely identifiable and distinguishable as per individual fiber optical strand 102 despite its presence in the preformed collective body 106 of the unitary fiber optical array 100.

It will be recognized and appreciated also that the overall organization of the individually clad, optical fiber strands 102 within the unitary array 100 is as aligned, parallel, strands which maintain its relative organizational positioning in a coherent, consistently aligned manner over the entire length of the collective body 106. This is deemed to be the most desirable and most easily constructable organization scheme for the preformed optical fiber array of the present invention.

Although this highly organized, coherent, and rigidly aligned collective construction is deemed to be most desirable, this high degree of organizational alignment is not an absolute requirement for each and every embodiment of the unitary optical array. Alternative manufacturing practices allow for a more random disposition of the individually clad, optical fiber strands disposed co-axially along their lengths. Although less desirable, a partially random disposition and a completely random alignment of the optical fiber strands will also result in a unitary collective body of optical fibers and in proximal and distal collective ends which provide two discrete optic array surfaces. In such embodiments, however, an optical fiber strand 102 whose intended distal end would be found to be at numerical position "IJ" could randomly present a intended proximal end position designated as "1c". It will be recognized therefore that while the individually clad, optical fiber strands lie adjacent to one another along the entirety of their lengths—their position relative to one another, however, may vary in part or in whole thereby creating semi-coherent or incoherent alignments which vary in the randomness of their organizational construction. There is no requirement that the positioning of the intended proximal end of one strand be aligned and/or identical with the positioning of the intended distal end within the unitary optic array. In such randomly organized optical array constructions, therefore, the precise proximal and distal end positioning for the strand end faces would be measured and identified by passing light energy through individual optical fibers at one optic array end and empirically determining the location of the light energy photons exiting from the other end of the same single fiber strand. Although far more laborious and inconvenient, by performing this extra step of empirically coordinating the proximal and distal ends of each individual optical fiber strand in the unitary array, an analogous exact set of numerical coordinates identifying the precise spatial positioning of the fiber at each end of the array may be obtained.

The entirety of the construction for the unitary imaging optical fiber array (whether uniformly coherent, semi-random, or completely randomly organized) provides a means of introducing light energy photons of any determinable wavelength at one specific position on one optic array surface and then be able to predict accurately the spatial position of the existing light energy at the other optic array surface. Therefore, by using the preferred completely coherent and rigidly maintained parallel alignment of strands illustrated by FIGS. 5 and 6 (the intended distal and proximal optic array surfaces respectively) of a unitary fiber optic array, the user may introduce light energy to a specific spatial location on the optic array surface 114—for example, only to fibers S1, S7 and S8—and have accurate knowledge and confidence that the light energy would be conveyed only by those three optical fiber strands and exit from numerical positions "XIID", "XIC", and "XID" alone on the optic array surface 112. No other light energy would appear from any other spatial position from the optic array surface 112. Similarly, were light energy of specific wavelengths introduced at the optic array surface 112 via fibers S107, S108, and S115 respectively, the user can accurately predict and identify that the light energy will be conveyed by only these three optical fibers; and will exit only at the optic array surface 114 of numerical coordinate position numbers 2c, 2d and 1d respectively and from no other spatial positions on this optic array surface. In this manner, not only does one have knowledge of the individual spatial positioning of each optical fiber strand in the preformed array but also one has the ability to identify and precisely locate light energy photons emerging from individual optical fiber strands within the whole of the optic array surface in a practical and reliable mode.

Accordingly, the critical and essential requirements of any optical fiber array construction allows and demands the capability for precise spatial positional introduction and conveyance of light energy via different fiber optical strands within the collective body of the preformed, unitary fiber optical array. This capability to introduce light energy photons at precise spatial positions at one optic array surface of a unitary array: to convey the introduced light energy along the length of only a few fiber optical strands; and to control the exit of the conveyed light energy at a second, precisely known, spatial position on the other optic array surface of the unitary array is the hallmark and essence of the singular fiber optic sensor presented herein.

B. The Dye Sensing Zone Comprising Light Energy Absorbing Dyes and Dye Mixtures.

The unique fiber optical sensor of the present invention requires that one or more light energy absorbing dyes be disposed individually at fixed spatial positions within a dye sensing zone upon one optical array surface of the unitary fiber optic array. It is the individual spatial positioning of one or more dyes separately within a discernable dye sensing zone upon the discrete, optical array surface which serves to identify and distinguish each dye from all other light energy absorbing dyes concurrently disposed on the same optic array surface; and which also provides the spatial resolution among the disposed dyes which avoids and eliminates random intermixing of individual light energy photons to and from each respective dye.

Within the dye sensing zone, each spatially positioned dye is disposed at an individual location on the optic array surface; will react with only one ligand or analyte of interest; and then show evidence of such reactive contact by either absorbing and reflecting a portion of the light energy or absorbing light and then subsequently emitting light energy of a different wavelength in return. Such reflected or emitted light energy is conveyed via those individual fiber optic strands in aligned position with the immobilized dye itself. Such conveyed light will emerge from the other optic array surface only at precisely located spatial positions; and thus be distinguishable as such from other light energy conveyed by other fiber optical strands via the precise spatial positioning and the spatial resolution of the emerging light at the optic array surface. In this manner, the conventional limitations and demands of single channel optical fibers are eliminated since the strands within the imaging fiber optical array retain the spatial positioning for each of the disposed dyes. Thus, the traditional requirement for spectral resolution is removed due to the ability by the imaging fiber optical array to resolve each of the dyes spatially.

Within the dye sensing zone, the dyes which may be employed and disposed individually at different precise spatial positions upon one optic array surface of the imaging fiber optical array are all conventionally known and often commercially available. The present invention intends that all the commonly useful properties and capabilities of the various classes of light energy absorbing dyes be employed as needed or desired for the specific use or application. Merely illustrative of the many different dyes are those fluorophores, fluorescent enzyme substrates, fluorescent antibody conjugates, and chromophores listed below within Tables I and II respectively.

TABLE I

| Compounds | Excitation Wavelength (λ range or maximum) | Fluorescence emission range (λ max) |
|---|---|---|
| A. Fluorophores | | |
| Eosin | 520–530 nm | 530–580 nm (550 nm) |
| TRITC-amine | 555 nm | 570–610 nm (590 nm) |
| Quinine | 330–352 nm | 283–450 nm |
| Fluorescein W | 488–496 nm | 530 nm |
| Acridine yellow | 464 nm | 500 nm |
| Lissamine Rhodamine B Sulforyl Chloride | 567 nm | 580 nm |
| Erythroscein | 504 nm | 560 nm |
| Ruthenium | 460 nm | 580 nm |

TABLE I-continued

| Compounds | Excitation Wavelength (λ range or maximum) | Fluorescence emission range (λ max) |
|---|---|---|
| (tris, bipyridium) Texas Red Sulforyl Chloride | 596 nm | 615 nm |
| B - phycoerythrin | 545,565 nm | 575 nm |
| Nicotinamide adenine dinucleotide (NADN) | 340 nm | 435 nm |
| Flavin adenine dinucleotide (FAD) | 450 nm | 530 nm |
| Carboxy Seminaphthorhodafluor | 587 nm | 640 nm |
| Naphthofluorescein | 594 nm | 663 nm |
| B. Fluorescent Enzyme Substrates | | |
| Fluorescein mono-B-D-glacto-pyranoside | 452 nm | 518 nm |
| Resorufin B-D-glucuronide | 468 nm | 584 nm |
| 8-acetoxypyrene-1,3,6-trisulforic acid trisodium salt | 368 nm | 391 nm |
| Coenzyme A (1-pyrene butanoic acid) ester | 339 nm | 377 nm |
| Fluo-3; freeacid [Molecular Probes, Eugene, CA] | 506 nm | 526 nm |
| Quin-2, tetrapotassium | 352 nm | 492 nm |
| Fluorescent Antibody Conjugates | | |
| Texas Red goat anti-morse Fg G conjugates | 590 nm | 615 nm |
| Protein A fluorescein conjugates | 480 nm | 520 nm |
| Anti-Atrazine fluorescein Conjugates | 480 nm | 520 nm |
| Anti-digoxin Texas Red Conjugates | 590 nm | 615 nm |

TABLE II

| Chromophore S | Energy Absorbance Range (λ max) |
|---|---|
| Iron-salicylate complex | 530 nm |
| Indamine dye | 590 nm |
| INT formazon dye | |
| Hopkins-Cole dye | 560 nm |
| Quinone-imine dye | 500 nm |
| Fe(SCH)′2 | 460 nm |
| Malachite Green | 620 nm |
| 4-bromo A-23187, freeacid | 340 nm |
| Cresol red | 415 nm, acid 570 nm, base |
| Phenophthalein | 600 nm |
| Oxine blue | 450 nm, acid; 600 nm, base |
| diphenylcarbazone disulphonic acid | 575 nm |
| Chrome bordeaux B | 575 nm |
| Calmagite | 650 nm |
| Ninhydrindye | 650 nm |

It will be recognized and appreciated also that the range, variety, and diversity of light energy absorbing dyes, dye formulations, and dye mixtures is not dependent upon a single light source or light energy supply in order to be effective. Although light energy of determinable wavelengths is desirably provided by electrical light sources—that is, light emitting diodes (LED's), lasers, laser diodes and filament lamps whose bands of light energy are typically controlled and selected by filters, diffraction gratings, polarizing filters; or alternatively broken into various broad wavelengths of light energy via prisms, lenses, or other optical/spectral articles, these are not exclusively the only source of useful light energy. Clearly, in various applications and circumstances chemical light energy, bioluminescence, and other less typical or conventionally employed light energy sources are deemed to also be useful. Accordingly, neither the true source nor nature of light energy photons nor the manner in which they are conveyed or otherwise caused to be created is of importance or consequence.

In addition, the spatially positioned dye individually may comprise other materials and chemical compounds for photo reactive contact. Thus each spatially positioned dye individually may in fact be formulated as a mixture of both light emitting and light absorbing dyes; and also comprise a variety of other light energy sensitive compounds made conventionally which are able to interact with specific dye properties. Merely exemplifying the nature of such multiple dye formulations and combinations are those described and claimed within copending U.S. patent application No. 294,175 filed Jan. 6, 1989 entitled "Fluorescence Intramolecular Energy Transfer Conjugate Compositions and Detection Methods"; now allowed as U.S. Ser. No. 762,245 filed Sep. 19, 1991 as well as the compositions described within U.S. Pat. No. 4,872,746 issued Apr. 18, 1989—the texts of which are individually expressly incorporated by reference herein.

Immobilizing dye mixtures

When depositing the individual dye(s) at precisely spatially positioned locations on one optical array surface, it is necessary that the dye formulations remain immobilized at the individual spatial positions assigned to each of them individually, without migrating towards any other position. Multiple methods of dye deposition and immobilization are conventionally known. Thus, one may prepare a specific fluorescent or colorimetric dye formulation comprising one or more dyes and other chemical compounds; and dispose the dye formulation at a specific spatial position and location on the optical array surface. Among the conventional practices of dye deposition a variety of polymerization processes are known, including thermal techniques, ionization methods, plasma methods, and electroinitiation procedures. These different methodologies are exemplified by the following publications, the text of each being expressly incorporated by reference herein. Thermal methods: Graham et al., *J. Org. Chem.* 44: 907 (1979); Stickler and Meyerhoff, *Makromal. Chem.* 179: 2729 (1978); and Brand et al., *Makromol. Chem.* 181: 913 (1980). Fonization methods: A. Chapiro, *Radiation Chemistry of Polymer Systems* Chapter IV, Wiley—Intersciences, Inc., New York, 1962; J. E. Wilson, *Radiation Chemistry of Monomers, Polymers, and Plastics,* chapters 1-5, Marcel Dekker, New York, 1974. Plasma Methods: Yasuda, W. and T. S. Hsu, *J. Polym. Sci. Polym., Chem. Ed.* 15: 81 (1977); Tibbett et al., *Macromolecules* 10: 647 (1977). Electroinitiation methods: Pistoria, G. and O. Bagnarelli, *J. Polym. Sci Polym, Chem. Ed.* 17: 1001 (1979); and Philips et al., *J. Polym. Sci. Polym. Chem. Ed.* 15: 1563 (1977).

The preferred method of dye disposition and immobilization is via the process known as photoactivation; and employs one or more photoactivated monomer preparations in admixture with one or more pre-chosen light energy absorbing dyes as a photopolymerizable formulation. Such monomer preparations typically comprise solutions of several monomers in admixture and a concentration of at least one light energy absorbing dye conjugated to an organic carrier which can be chemically cross-linked. A representative listing of different monomer compositions suitable for preparing an admixture which subsequently can be photopolymerized are given by Table III; and an illustrative listing of conjugated dyes ready for admixture and photopolymerization is given by Table IV below.

TABLE III

| A. Monomers |  |
|---|---|
| acrylamide |  |
| N,N-methylene bis (acrylamide) |  |
| hydroxyethylmethacrylate |  |
| styrene |  |
| vinyl acetate |  |
| (N-(3-aminopropyl) meth-acrylamide hydrochloride [Kodak, Inc.] |  |
| B. Comonomer with dimethylsiloxane |  |
| (acryloxypropyl) methyl | (15-20%) |
| (aminopropyl) methyl | (3-5%) |
| (methacryloxypropyl) methyl | (2-3%) |
| C. T-structure polydimethylsiloxanes |  |
| methacryloxypropyl | (25-50%) |
| vinyl | (50-75%) |

TABLE IV

| Conjugated dye |
|---|
| acryloyl fluorescein |
| acryloyl rhodamine |
| acryloyl eosin |
| phenolred acryloyl |
| 8-hydroxypyrene 1,3 disulfonic acid acryloyl |
| seminaphthorhodafluor acryloyl |

TABLE IV-continued

| Conjugated dye |
|---|
| seminaphthofluorescein |

It will be appreciated that the listings of Table III and Table IV ar merely representative of the many different substances which can be usefully employed in admixture with one or more light energy absorbing dyes. In addition, the scientific and industrial literature provides many alternative monomer preparations and admixtures which are also suitable for use in making the present invention. Accordingly, all of these conventionally known monomer preparations are considered to be within the scope of the present invention.

II. A Preferred Method of Making the Fiber Optic Sensor

To demonstrate a most desirable method of making the unique fiber optic sensor comprising part of the present invention; and as a demonstration of the utility and effectiveness for making optical determinations using the fully constructed fiber optic sensor, a detailed description of the manipulative steps for making a sensor able to concurrently measure both pH and oxygen concentration is presented. It will be expressly understood, however, that the detailed description which follows hereinafter is merely illustrative and representative of the many different kinds of sensors which can be made having one or more dyes disposed at precise spatial positions on one optical array surface, each disposed dye being able to react with and individually detect one ligand or analyte of interest in a fluid sample. The dyes employed as described herein have been chosen for their ability to detect and accurately measure analytes which are correlated with changes in pH and changes in oxygen concentration.

Surface silanization

Initially, an imaging fiber optic array similar to that illustrated by FIGS. 4–6 respectively was obtained from commercial sources [Applied Fiber Optics Inc., Southbridge, Mass.]. One optical array surface was submerged in a 20% solution of 3-(trimethoxysilyl) propylmethacrylate dispersed in dry acetone and allowed to soak for 2 hours duration. After silanization, this optical array surface was rinsed first with dry acetone and then with distilled water. The prepared optical array surface of the imaging fiber optic array was used within one hour's time in the photopolymerization process.

Imaging fiber connections

A fiber optic connector and ferrule [AMP, Inc., Harrisburg, Pa.] were modified to physically secure the imaging fiber optic array to a fiber optic cable able to transport light energy of varying wavelengths to precise spatial positions on the distal array surface of the imaging fiber optic array. The exterior surface of one representative lighting cable is illustrated in an enlarged view by FIG. 7.

Figure 7:
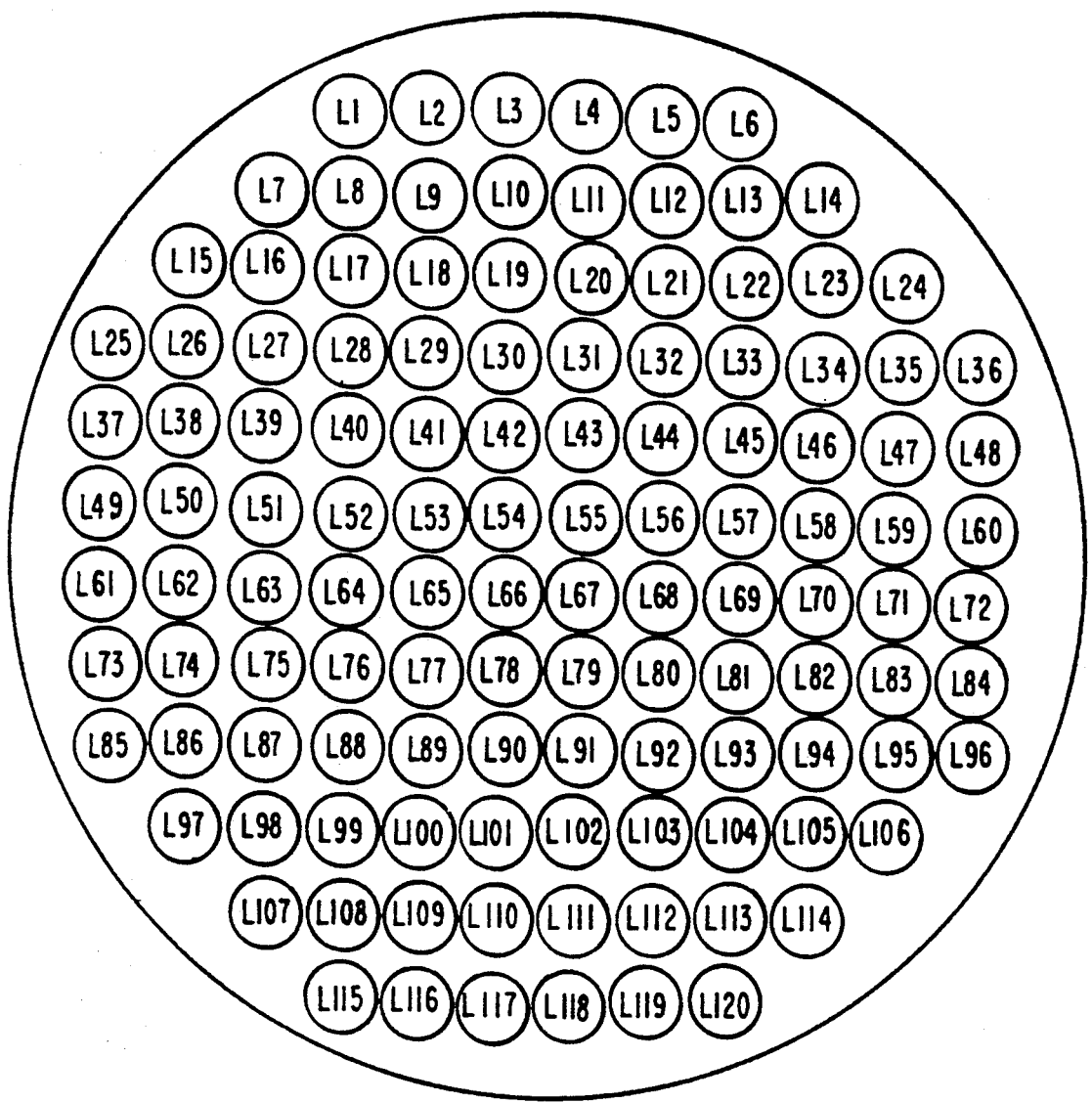
FIG. 7 is a frontal view of an illumination source able to provide light energy at precise spatial positions concurrently.

An inspection of the lighting cable of FIG. 7 reveals (in an exaggerated, highly oversimplified view for purposes of clarity) that the individual light sources via coordinated numerals correspond precisely to the spatial positions of FIGS. 5 and 6; and are directly aligned with individual fiber optical strands S1–S120 (which also are precisely positioned spatially and identifiable via linear coordinates). Thus, light originating from source L1 will be introduced only to fiber S1 spatially positioned at coordinate number "12a"; similarly, light energy emanating from source L85 will be introduced only to that precise spatial position on the proximal optical array surface identifiable as fiber S85 at coordinates "4a". In this manner, only predetermined and prechosen fiber optical strands will receive light energy of determinable wavelengths for a specified duration; at a time desired by the user alone; and no other optical fiber strand will receive any light energy whatsoever other than those strands located at a precise spatial position on the surface of the optic array surface. By purposeful choosing, therefore, of which light sources on the lighting cable are to be employed, the user may introduce light energy at will to only pre-chosen, precise spatial positions and only to those few fiber optical strands known to be present at precisely that location alone on the optical array surface.

In most practical use instances, however, the lighting cable of FIG. 7 will not be employed because of its limitations. Recognizing that the typical cross-sectional diameter of a single fiber optical strand is only 2–20 micrometers; and recognizing further that the dye to be deposited precisely at a known spatial position on the optic array surface will desirably provide and encompass a surface area far greater than the diameter of a single fiber strand; then clearly it is impractical and functionally unnecessary to employ only a lighting cable of such limited one-to-one correspondence as that shown by FIG. 7.

In actual practice, therefore, a lighting apparatus having a pinhole in a filter holder which allows fine focusing and precise placement of light is employed in the making of the pH and oxygen sensor hereof. This pinhole apparatus has only one light source of illumination rather than a cable having multiple light sources; and the single pinhole acts as a light source to introduce focused light energy to several dozen individually clad, optical fiber strands simultaneously—all the simultaneously illuminated strands being adjacently positioned within the imaging fiber optic array at precisely known spatial positions. In this manner, the single pinhole light source corresponds to and aligns with multiple fiber strands simultaneously; and permits the deposition of a dye over multiple strand faces simultaneously. The advantages and benefits of using the single source of focused lighting are that a controlled volume of dye is precisely deposited at the pre-chosen spatial position on the optic array surface with minimal time and labor.

The lighting cable of FIG. 7, although completely operational for its intended purpose, is far too cumbersome for practical use; is provided only as a representative article to demonstrate the principle of introducing light energy to a precise location on the proximal optic array surface; and is used merely to illustrate the method and the manner in which the dye becomes photopolymerized and precisely positioned at a pre-chosen location on the distal optic array surface. Having illustrated both the principle and the intended result, it will be recognized and appreciated that any lighting source of any correspondence with the fiber optical strands of the imaging fiber optic array will serve so long as the disposed dyes are spatially separate and spatially distinguishable from one another on the optic array surface.

Monomer preparations

The pH sensing dye admixtures were formulated as follows: Aqueous solutions of 5.63 M acrylamide and 0.0746 M N,N-methylene bis(acrylamide) were prepared in phosphate buffer solution (pH 6.6). A typical stock solution comprised 5.0 mls of bis(acrylamide), 3.0 mls of acrylamide, 5.0 mg of riboflavin, 10 mg of acryloyl fluorescein, preferably prepared in a glass container. The stock solution was then deoxygenated by bubbling molecular nitrogen into the prepared mixture for one hour's duration. In addition, a fresh catalyst solution was prepared by dissolving 40 mg of ammonium persulfate in 0.05 ml of pH 6.6 phosphate buffer. Subsequently, the final admixture is made by combining 3.0 ml of the stock solution and 0.5 ml of the prepared catalyst solution.

As a useful and desirable alternative monomer preparation, the individual solutions are prepared as described previously above, except that 2 mg of acryloyl tetramethylrhodamine may be substituted for the 10 mg of acryloyl fluorescein.

The oxygen sensing dye admixtures were formulated as follows: 10 ml of methylacryloxypropyl T-structure [Petrarch Systems, Bristol, Pa.] was combined with 100 mg of camphorquinone in 1 ml of methanol and 10 mg of tris (2,2'-bipyridyl ruthenium (II) chloride hexahydrate [Aldrich Company, Milwaukee, Wisc.] in 1.0 ml of methanol. This prepared stock solution was then deoxygenated by bubbling molecular nitrogen through the preparation for one hour's duration. Approximately 3.0 ml of the prepared stock solution was then employed for polymerization purposes.

Photopolymerization

The manipulations performed during photopolymerization are illustrated via FIGS. 8–13 respectively. For descriptive purposes only, the greatly magnified and oversimplified construction of the optic array surface of FIG. 5 and the lighting cable of FIG. 7 will again be used.

Figure 8:
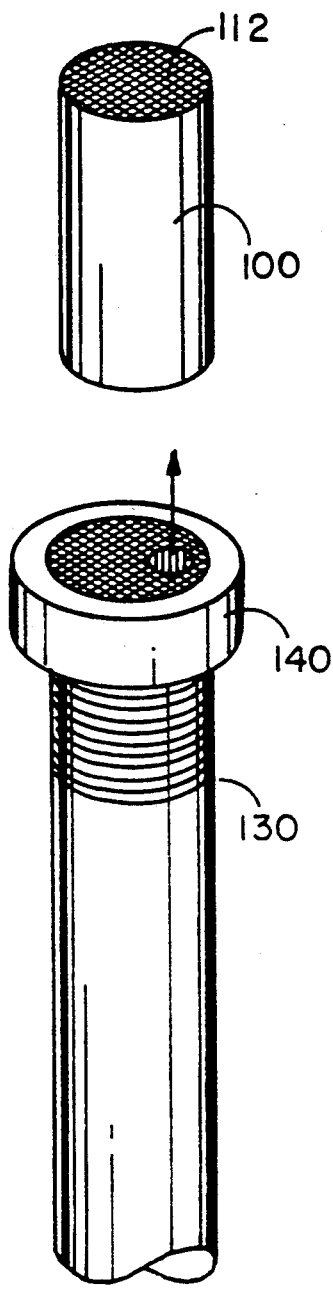
Figure 9:
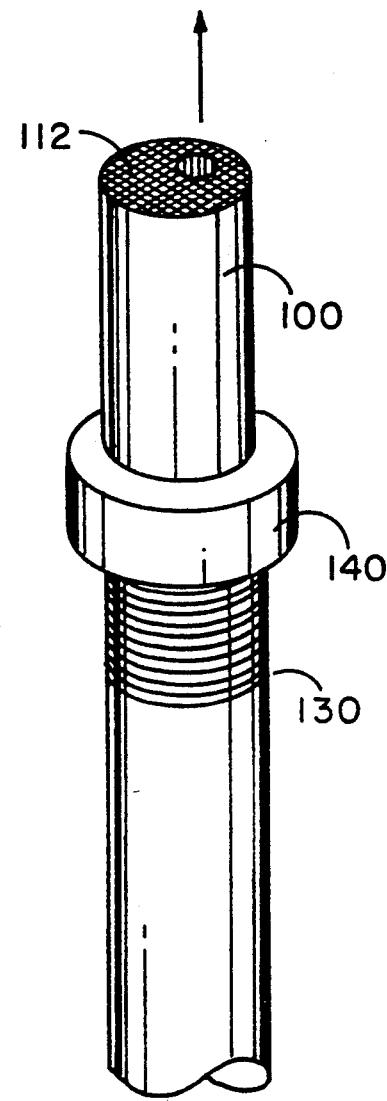

As seen within FIGS. 8–13, a fiber optical connector 130 and illumination source 140 provide the capability for illuminating specific areas of one optic array surface of the imaging fiber optic array described previously. Thus, the light energy photons emanating from the surface of the illumination source 140 of FIG. 8 are produced by only light sources L1, L7, L8, L15, L16, L25, L26 and L27, L28 respectively. Only light energy at those precise spatial positions is directed towards the distal optic array surface 114 of the unitary fiber optical array 100. Consequently, as shown via FIG. 8 only those fiber optical strands located at spatial position coordinates 12d, 11c, 11d, 10b, 10c, 10d, 9a, 9b, 9c and 9d respectively receive the light energy photons provided by the illumination source 140. Then as illustrated by FIG. 9, only those corresponding individually clad fiber optical strands (S1, S7, S8, S15, S16, S17, S25, S26, S27 and S28) convey the introduced light energy through the body of the unitary fiber optical array 100; and the light exits at the optic array surface 112 only at precise spatial positions (that is, solely at coordinate numbers XIID, XIC, XID, XB, XC, XD, IXA, IXB, IXC and IXD) as seen within FIG. 5 above. It will be recognized and appreciated that no other spatial positions on the distal array surface 112 are illuminated during this manipulation.

The first polymerization step:

As the light energy photons emerge from the distal array surface 112 at only the precise spatial positions indicated by FIG. 9, the optic array surface 112 is submerged in the prepared pH sensing dye monomer admixture comprising acryloyl fluorescein. The light employed at only this precise spatial positioning zone employed was 370 nm light and the optic array surface was allowed to react with the monomer preparation for approximately one hour's duration. The reactive contact between the pH monomer admixture and the 370 nm light initiated a photopolymerization reaction which caused a deposition and an immobilization of the fluorescein dye only at those illuminated spatial positions on the proximal array surface. Thus, at the end of the allotted reaction time for photopolymerization, a discrete cone-shaped volume 150 of polymerized fluorescein dye was deposited and immobilized solely on the optic array surface at only these precisely 3d, 2c, 2d, and 1d. This, in turn, caused the introduced light energy photons to be conveyed solely by fibers S85, S86, S87, S88, S97, S98, S99, S107, S108 and S115. No other fiber strands were illuminated and no other fiber strands conveyed any light energy whatsoever. This is illustrated by FIGS. 11 and 12 respectively.

Figure 12:
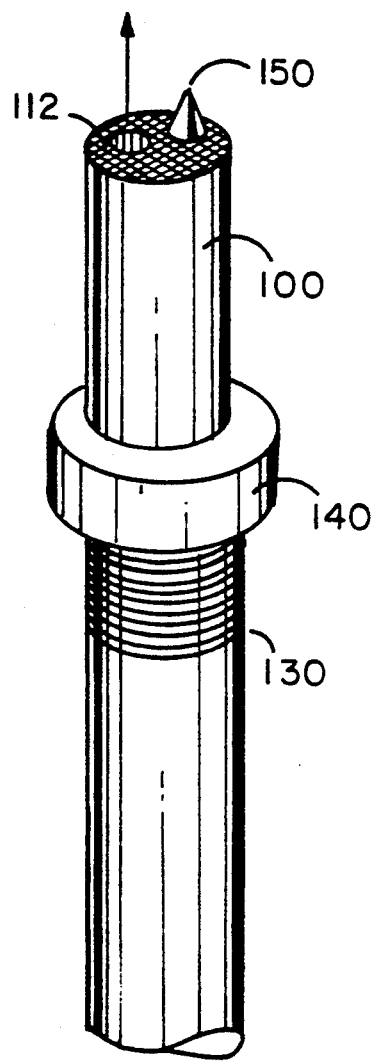
Figure 13:
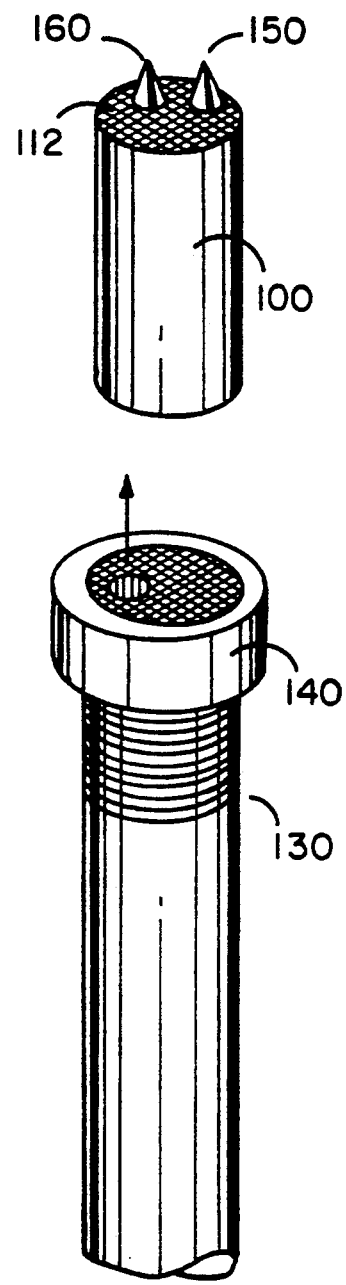

Consequently, as appears in FIG. 12, light energy photons carried by only these individually clad, fiber optical strands cause the light to be conveyed and to exit from the optic array surface 112 of FIG. 5 only at coordinate position numbers IVA, IVB, IVC, IVD, IIIB, IIIC, IIID, IIC, IID, and ID. The light wavelengths appearing at only these precise spatial positions on the optic array surface was 370 nm. The optic array surface was then immersed in the prepared oxygen sensing dye monomer mixture and the light energy allowed to react with the prepared mixture for 2 minutes duration. During this reaction time, photopolymerization proceeded and the ruthenium dye in the mixture was deposited solely at those spatial positions which were illuminated. In this manner, the ruthenium dye became immobilized by photopolymerization at only those precisely illuminated locations identifiable by the coordinate numbers. At the end of the allotted time for reactive contact, the distal optic array surface of the imaging fiber optic array was removed from the second monomer admixture and revealed the deposition of immobilized ruthenium dye at the precise spatial positions now identifiable precisely by coordinate numbers IVA, IVB, IVC, IVD, IIIB, IIIC, IIID, IIC, IID and ID. A discrete cone 160 of ruthenium dye could be seen extending from the proximal array surface as illustrated by FIG. 13.

It will again be recognized and appreciated that under typical conditions the density of fiber strand diameter in the imaging fiber optic array so overwhelmingly exceeds the amount of corresponding cladding material that there is no effective separation between the fiber strands during the photopolymerization process. Thus the photopolymerization of the ruthenium dye mixture at only the pre-chosen and illuminated spatial positions results in the deposition of a single, unitary continuous volume or cone of dye large enough in surface area to encompass and cover multiple fiber faces on the distal optic array surface. The presence of the cladding within the imaging fiber optic array does not interfere with or hinder the continuity of the dye deposition. The result is both true and constant regardless of what specific process for depositing dyes is employed and whether or not the favored photopolymerization technique is used.

The practitioner ordinarily skilled in this field will by now also recognize that there is no requirement or demand that an illumination fiber or cable as such be employed in this photoactivated method for making the sensor. To the contrary, one merely needs to introduce pinpoints of light into separate portions of areas of the imaging fiber optic array for photopolymerization to proceed. Thus, for example, one could achieve equivalent effects using lenses and/or lasers. Accordingly, any conventionally known means or manner of introducing light is deemed to be within the scope of the present invention.

Figure 14:
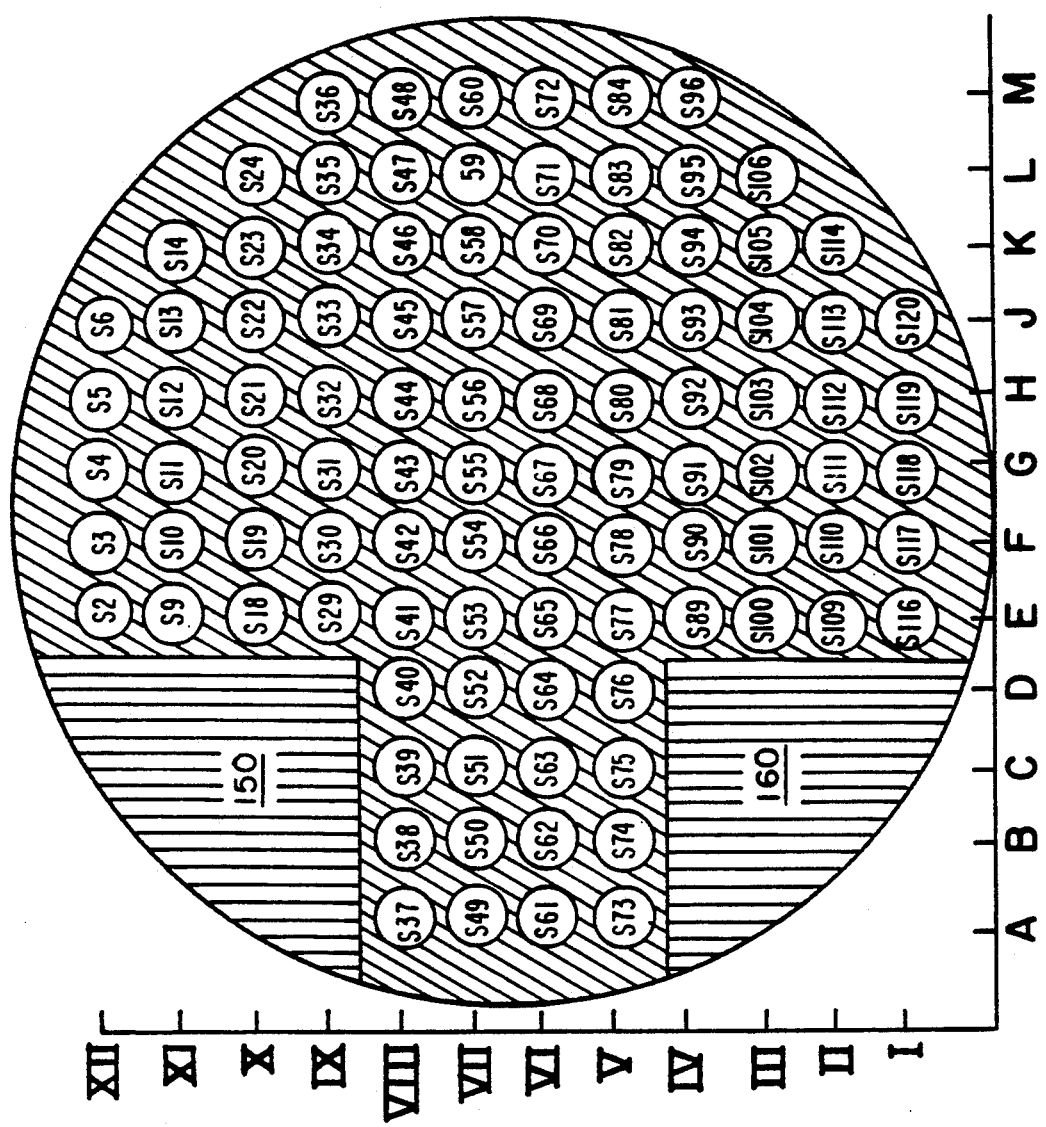
FIG. 14 illustrates a first arrangement of multiple uninterrupted dye deposits at different spatial positions on the distal optical array surface of FIG. 6.

The results of the completed photopolymerization process are illustrated by FIG. 14 in which the polymerized cone of fluorescein 150 and the polymerized cone of ruthenium dye 160 are individually located and identifiable at precise spatial positions in discrete dye sensing zones on the Optic array surface It will also be recognized that much of the distal optic array surface 112 remains unencumbered and unobscured; and that light introduced at the proximal array surface 114 at any of the unobscured strand spatial positions would be conveyed and would exit from the distal optic array surface as unencumbered light photons within a separate viewing zone which does not affect or influence the dye cones 150, 160 positioned separately nearby. Therefore, these regions can be used to view the volume directly in contact with these fiber faces.

III. THE DISCRETE VIEWING ZONE

The preferred photopolymerization process described herein provides a broad range and variety of dye sensing zones and unobscured discrete viewing zones on the distal array surface of the preformed, unitary optic array sensor. Illustrative of this construction is FIG. 14 which has been described in detail previously herein and shows dye cones 150 and 160 on the distal optic array surface 112.

Figure 15:
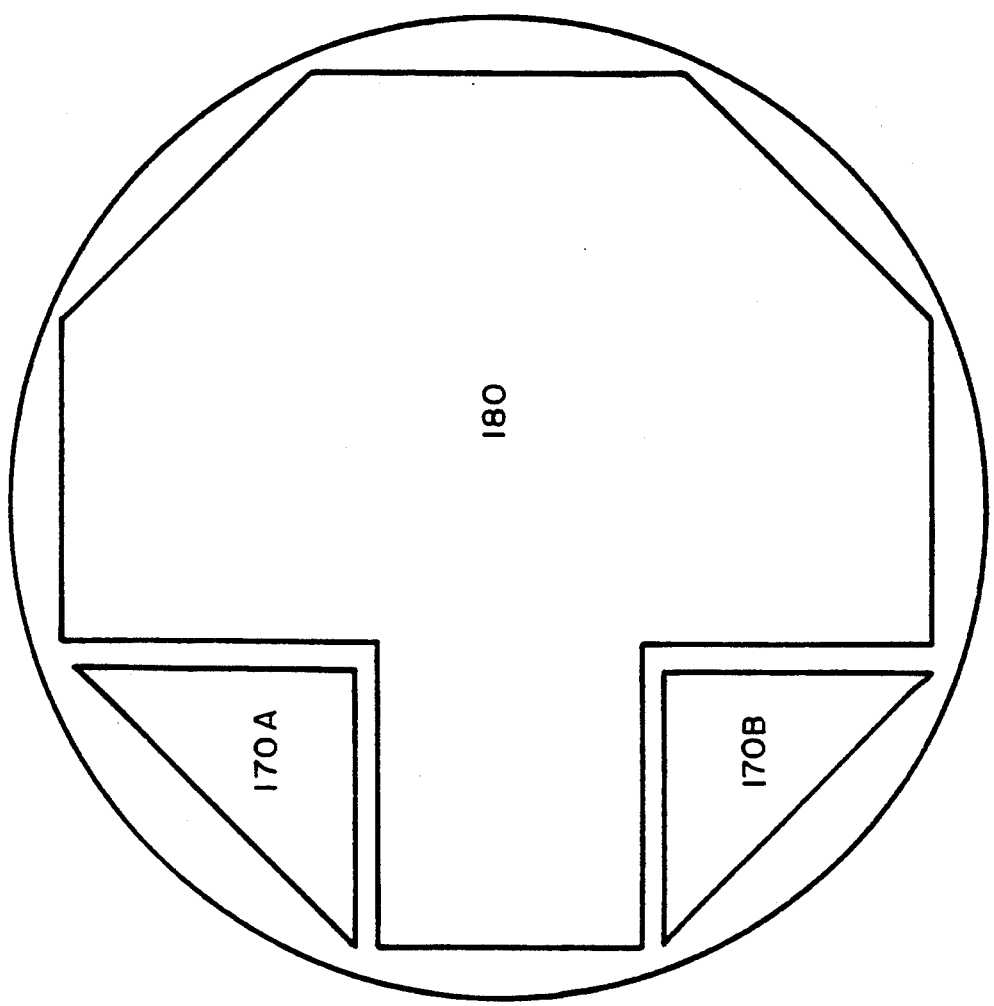
FIG. 15 shows a schematic representation of the dye sensing zone and the sample viewing zone for the arrangement of FIG. 14.

An alternative schematic representation of this same distal optic array surface is shown by FIG. 15 in which dye cones 150 and 160 collectively lie within and form a dye sensing zone 170 while the remaining unobstructed array surface serves as a sample viewing zone 180. Note that the dye sensing zone itself is formed of the two distinct parts 170a and 170b comprising the dyes 150 and 160 respectively. In contrast, the user may view the contents of the sample on-demand or at will by introducing light to the remainder of the optic array sensor formed by strands S2-S6, S9-S14, S18-S24, S29-S36, S37-S84, S89-S96, S100-S106, S109-114, and S116-120 respectively. These strands together provide a single viewing zone 180 on the distal array surface.

Figure 16:
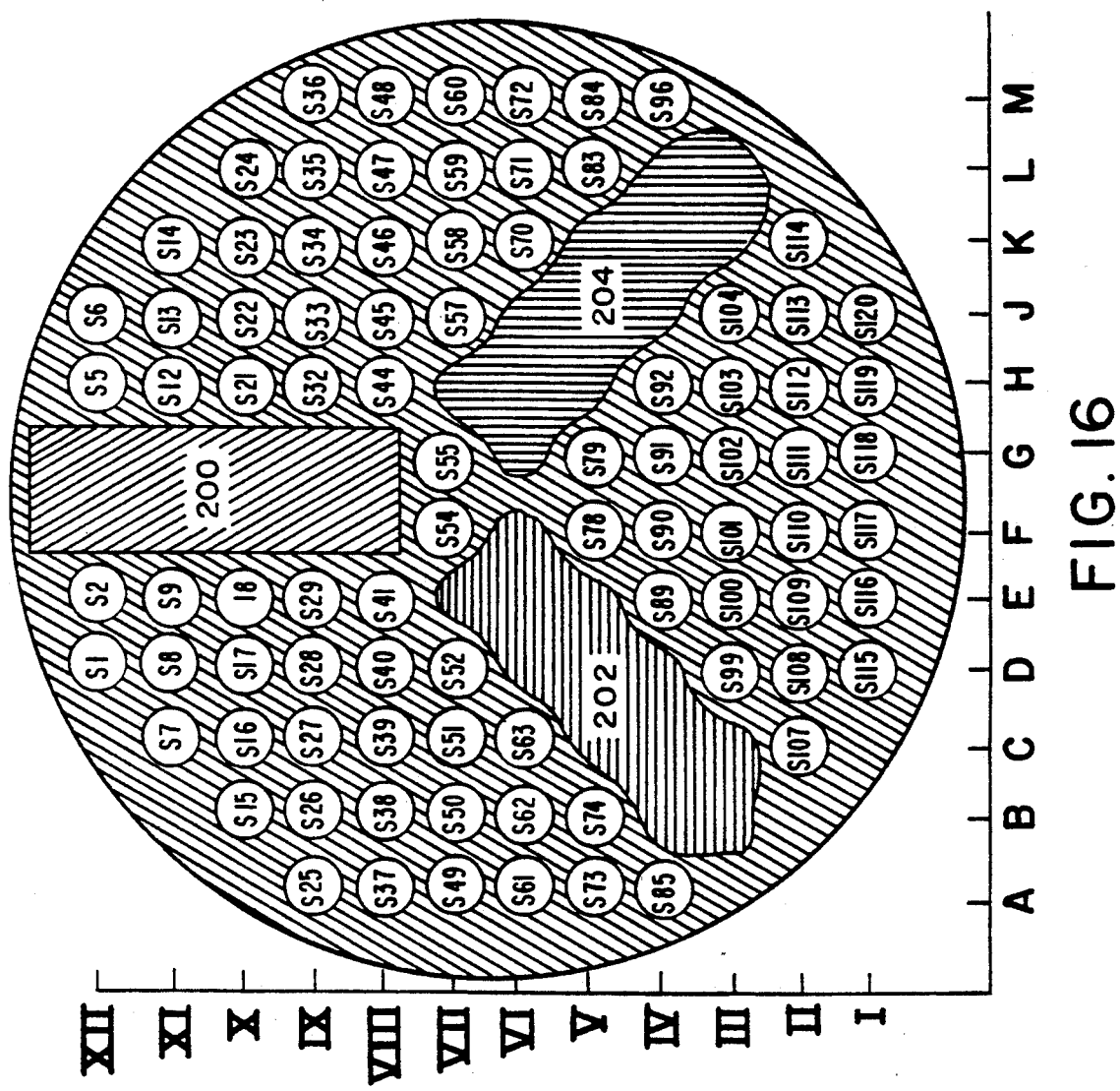
FIG. 16 illustrates a second arrangement of multiple uninterrupted dye deposits at different spatial positions on the distal array surface of FIG. 6.
Figure 17:
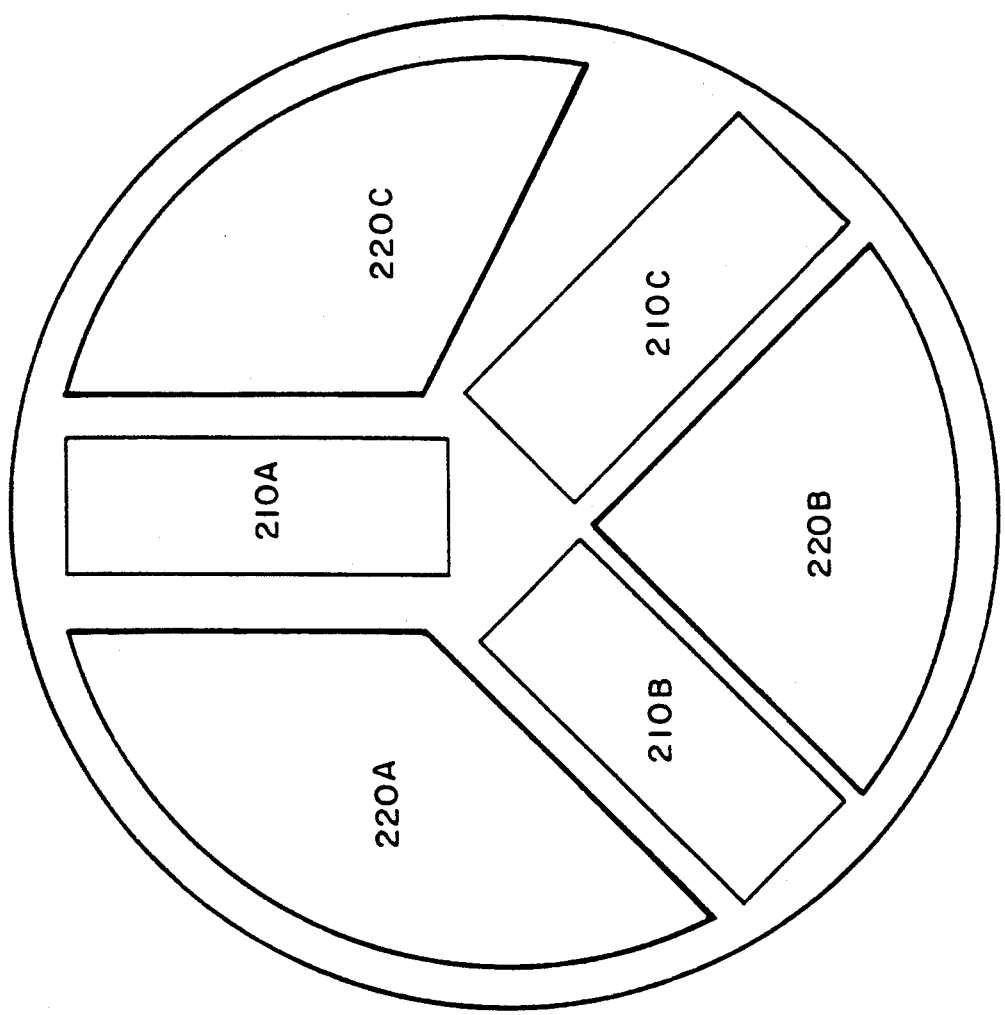
FIG. 17 shows a schematic representation of the dye sensing zone and the sample viewing zone for the arrangement of FIG. 16.

Another desirable arrangement of dye sensing zone and viewing zone is shown by FIGS. 16 and 17. In this format, three different uninterrupted dye deposits 200, 202 and 204 form and lie within the dye sensing zone 210. The dye deposits 200, 202, and 204 may be chemically alike for the detection of a single analyte; or be individually different for the detection of three different analytes independently. The remaining optical fiber strand faces in this distal array surface remain uncovered and are unobscured. These thus form a viewing zone 220 having three distinct areas 220a, 220b, and 220c. In this manner, the user may perform one or more analyte determinations concurrently with visual inspection and examination of the sample via any of the viewing zone areas.

Figure 18:
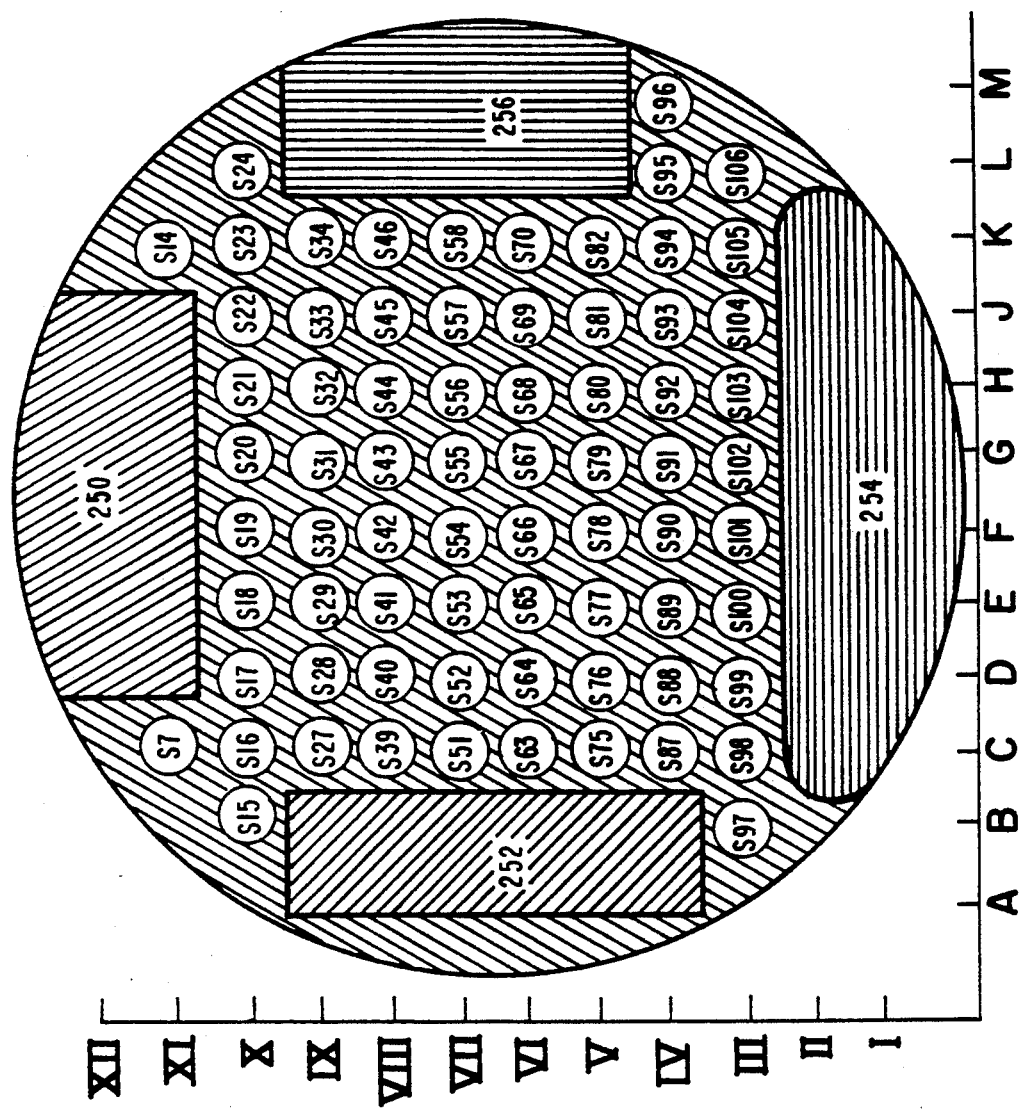
FIG. 18 illustrates a third arrangement of multiple uninterrupted dye deposits at different spatial positions on the distal array surface of FIG. 6.
Figure 19:
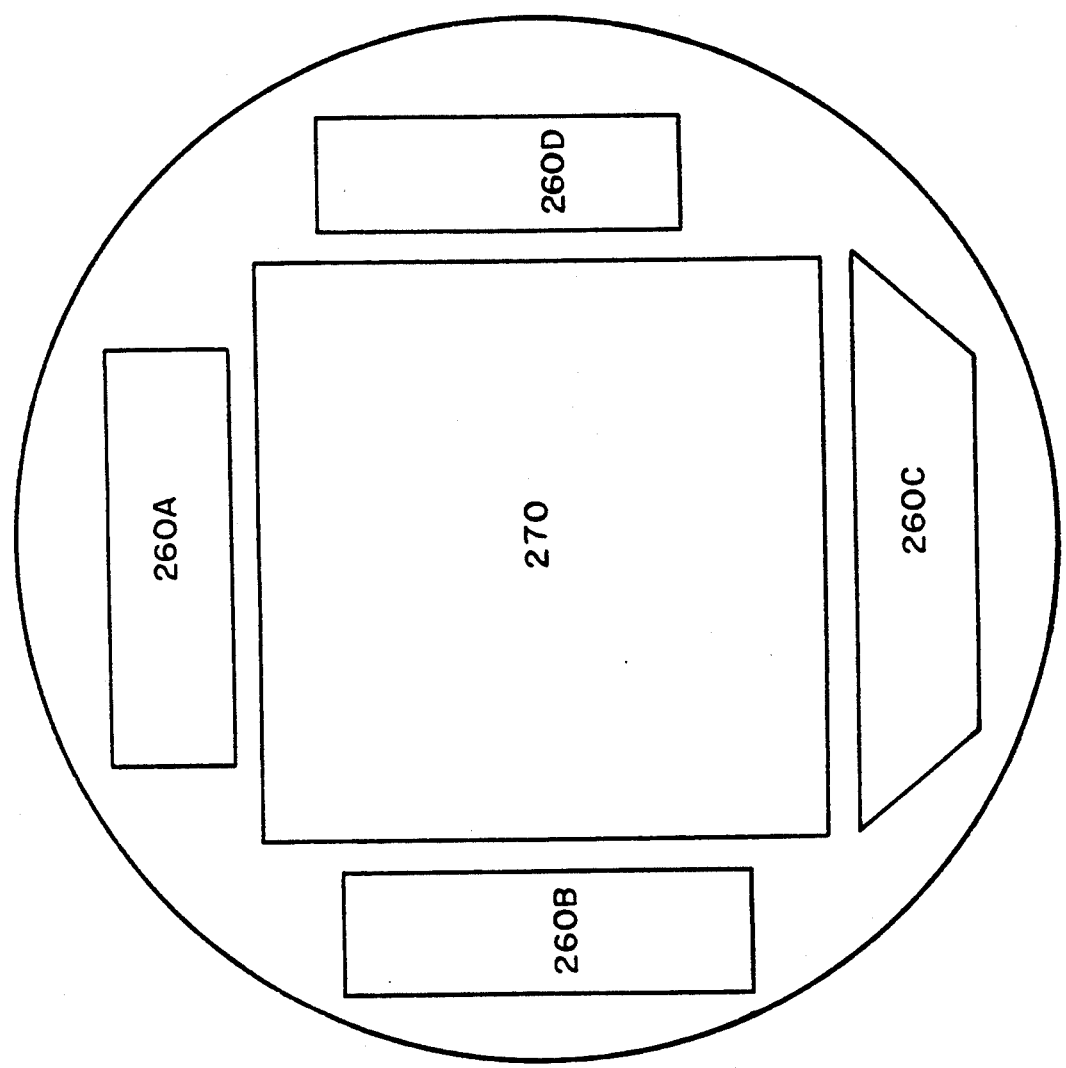
FIG. 19 shows a schematic representation of the dye sensing zone and the sample viewing zone for the arrangement of FIG. 18.

A third illustration of a desirable relationship between a dye sensing zone and a discrete viewing zone on the distal optic array surface of the unitary sensor is shown by FIGS. 18 and 19 In this example, four uninterrupted dye deposits 250, 252, 254 and 256 are individually positioned at the outer perimeter of the optic array surface. Collectively they comprise the dye sensing zone 260 for the sensor and desirably provide four different analytical determinations via areas 260a, 260b, 260c and 260d respectively. In the center of the optic array surface lies a single, substantially rectangular-shaped, viewing zone 270 for concurrent visual examination of the sample and the surrounding environment. By definition, the term "concurrent" includes the words "prior to", "simultaneously", and "after". Thus, the user may perform a visual examination of the sample and the adjacent location at will via the viewing zone of the sensor in accordance with his personal needs or desires.

Figure 20:
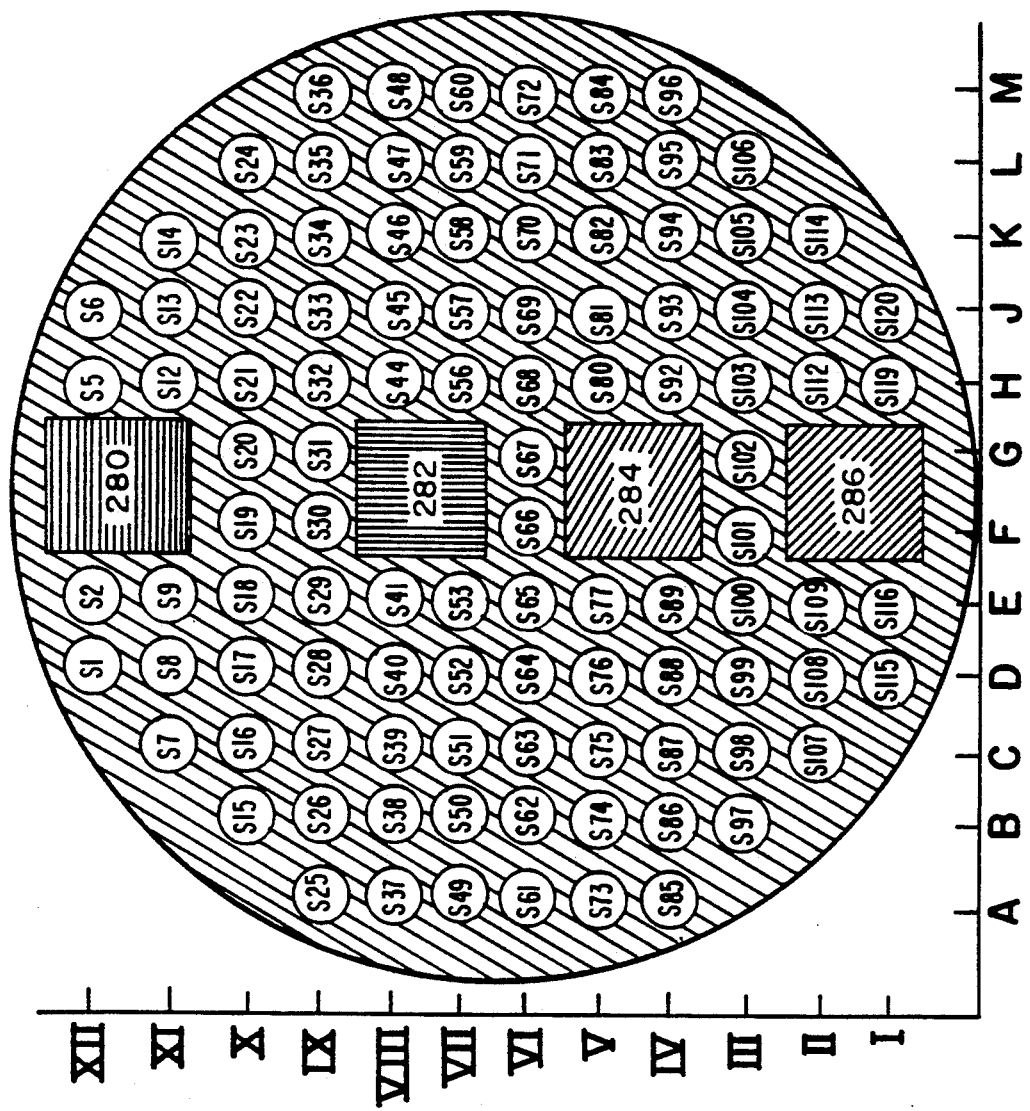
FIG. 20 illustrates a fourth arrangement of multiple uninterrupted dye deposits at different spatial positions on the distal array surface of FIG. 6.
Figure 21:
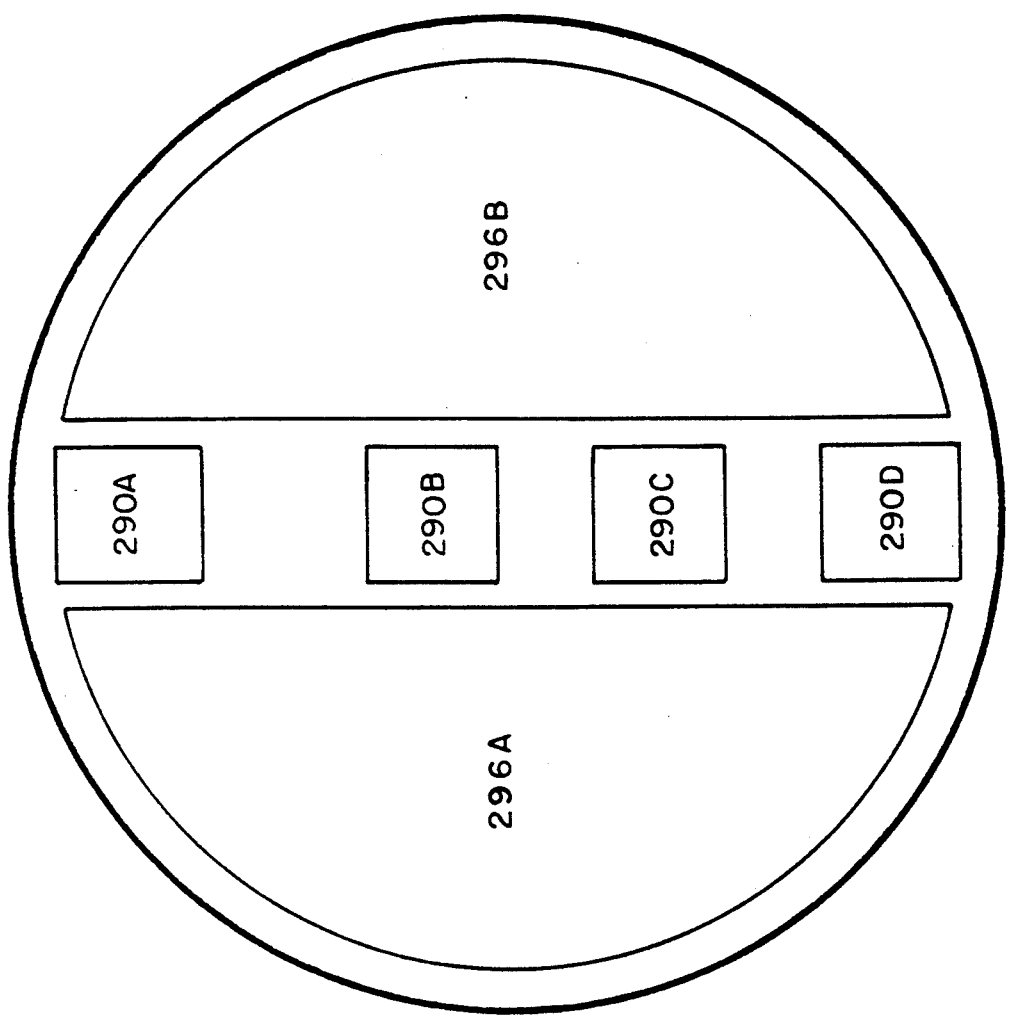
FIG. 21 shows a schematic representation of the dye sensing zone and the sample viewing zone for the arrangement of FIG. 20.

A fourth illustrative arrangement of dye sensing zone and viewing zone on the distal optical array surface is provided by FIGS. 20 and 21 respectively. Four uninterrupted dye deposits 280, 282, 284 and 286 are fixed in different spatial positions on the distal optical array surface and together form and lie within the dye sensing zone 290. Desirably, different chemical dyes comprise the areas 290a, 290b, 290c and 290d fixed linearly across the diameter of the optic array surface. The viewing zone 296 is formed by two distinct semi-circular areas 296a and 296b positioned on either side of the dye sensing zone 290.

It will be recognized and appreciated that FIGS. 14-21 are merely representative of the many different arrangements of dye sensing zones and viewing zones which can be prepared on the distal optic array surface. Clearly, the dye sensing zone may be formed with one or multiple dye deposits which individually or collectively are able to detect at least one analyte of interest. Similarly, the viewing zone can comprise one area or multiple areas for visual inspection of the sample and the immediately adjacent environment. Accordingly, any arrangement which provides at least one dye sensing zone and at least one viewing zone on the optical array surface is within the purview of the present invention.

IV. DETECTING APPARATUS EMPLOYING THE UNIQUE FIBER OPTIC SENSOR

Figure 22:
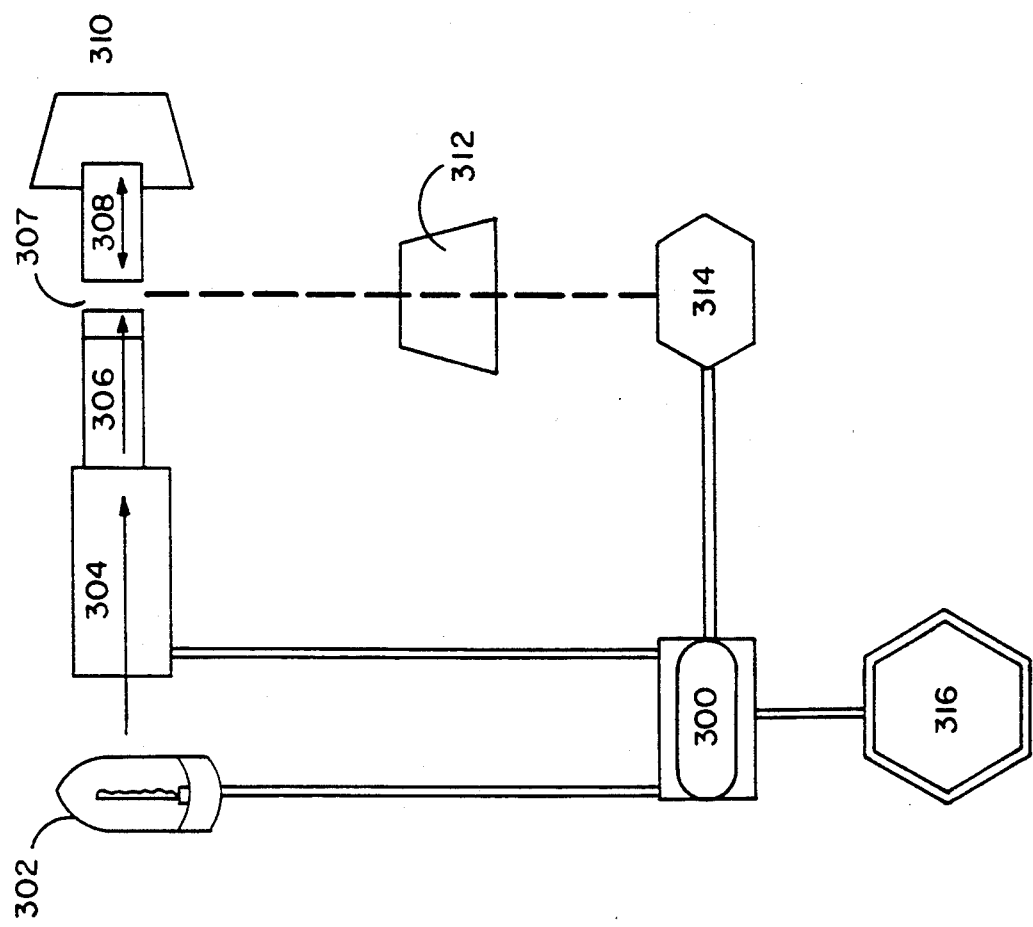
FIG. 22 is a schematic block diagram of the automated apparatus comprising the fiber optic sensor of FIGS. 14–21 respectively.
Figure 23A:
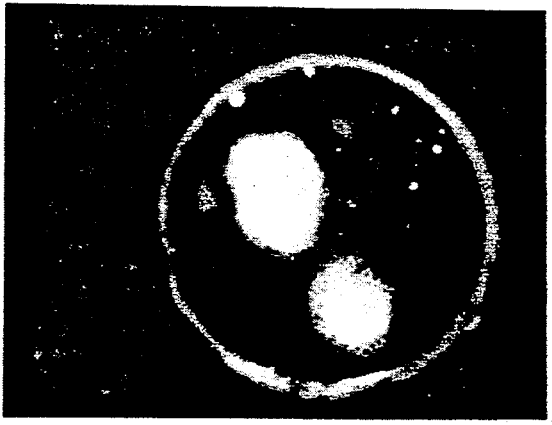
FIGS. 23A–23D are imaging photographs of the uninterrupted dye deposits of FIG. 14 after illumination using the apparatus of FIG. 23.
Figure 23C:
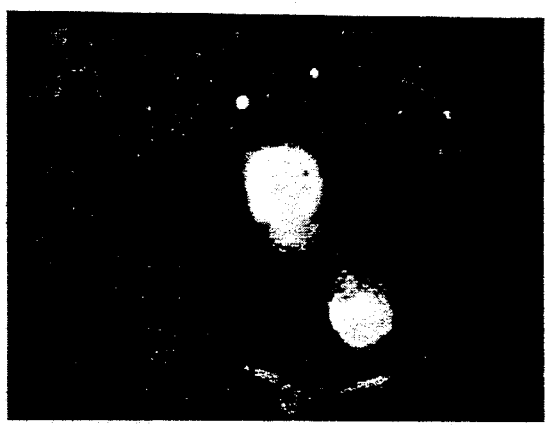
Figure 23B:
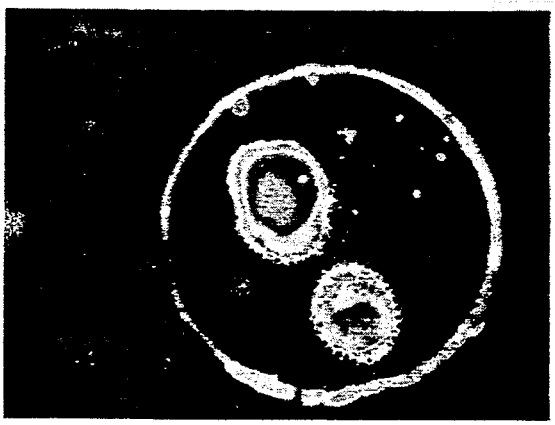
Figure 23D:
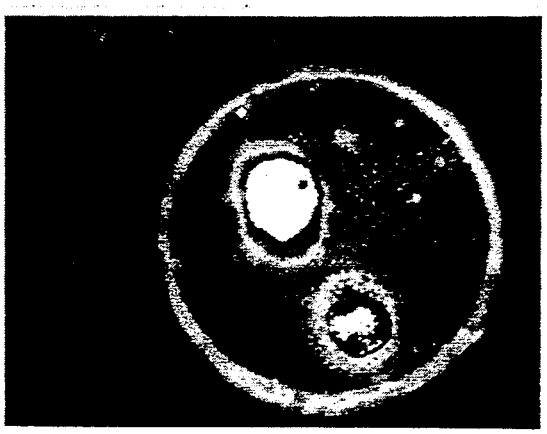

A preferred fully automated, computer controlled, apparatus and detection system is illustrated in block format by FIG. 22. As seen therein, a controller 300 serves to generate and control an image processing and detection system from the generation of light energy photons of a specific wavelength to the control and detection of optical images then measured in both qualitative and quantitative parameters. Such controllers are commercially available and provide software and hardware with a microprocessor and computer which allows the entire apparatus to be controlled from a single keyboard. Such a commercially available controller is the QX-7 image processing system [Quantex, Inc.] which provides monitors for both visual display and mathematical calculation of the optical data empirically detected and measured. The controller 300 controls a high-intensity light beam 302 which passes through a first monochromater or filter 304 for the selection of light energy of a predetermined wavelength The controller 300 then causes the first light energy photons to be directed via an optional fiber optic cable 306 to the proximal optic array surface of the fully constructed fiber optic sensor 308 which has one or more light energy absorbing dyes immobilized individually at separate and distinct precise spatial positions on the distal optic array surface The distal optic array surface of the fiber optic sensor 308 has been placed in a sample holder into which a fluid sample is introduced for reactive contact with the distal optic array surface of the fiber optic sensor. The introduced light illuminates the dye which has reacted with the analyte of interest within the sample holder 310.

As a result of the reactive contact between the dye disposed on the distal optic array surface of the fiber optic sensor 308 and the fluid sample in the holder 310 light energy emanating from the dye (by emission or reflection) is then conveyed through the fiber optic strands in the fiber optic sensor 308 and emerges at the proximal optic array surface as emergent light energy. The apparatus is desirably constructed with a beam splitter or dichroic mirror so that the emergent light energy is observed at right angles to the original incident beam of introductory light. The emergent light energy then passes through a second monochromater or filter 312 for wavelength analysis; and then falls upon a photosensitive detector 314 for qualitative and quantitative measurement of the photons present as the emerging light energy. The detector 314 typically is a camera. The detector 314 also is in direct contact with the controller 300 which mathematically calculates and plots the intensity of the emerging light as a function of its wavelength and quantum of photons present. The data and mathematical calculation are then preferably seen visually on a monitor display 316 which can provide a visual image of the dye reacting with the individual analyte of interest; and can also provide the empirical data in raw or mathematically calculated and correlated formats.

In many instances, the sample holder 310 will take form as a microscope or camera apparatus in addition to providing an enclosed chamber for reactive contact between the sensor and the analyte of interest in the fluid sample. Many other instruments may be optionally added at various positions in the automated system to provide detailed information as the user requires or desires.

It is also optionally available for the user to operate the image processing and detection apparatus and system manually at one or more positions if this is desired. Alternative assemblies may be erected in which the entire series of manipulative steps may be done manually for specific purposes of the experiment or analysis. In most instances and for general operation purposes, however, the fully automated, computerized imaging and processing system as described herein is most desirable.

The apparatus illustrated in block format via FIG. 22 intends that the light energy be introduced and conveyed concurrently to each of the individual dyes disposed within the dye sensing zone on the distal optic array surface of the fiber optic sensor. The true value and benefit of the fully automated apparatus and image processing system is that light energy of the same or different wavelengths will be precisely introduced at the proximal optic array surface of the optic fiber sensor; that only pre-identified and chosen fiber optical strands will convey that individual light energy to one immobilized dye situated precisely at a single spatial position on the distal optic array surface of the sensor after reactive contact with a fluid sample; and that the emerging light from the dye sensing zone from each immobilized dye after reactive content with its own individual analyte of interest would then be recognized via its controlled emergence from only precise spatial positions which allow it to be detected and measured independently without interference in the shortest possible time period The fully automated, computer controlled system thus allows multiple determinations, measurements and detections to be made within fractions of a second concurrently without accidental mixing or interferences between the emergent light at different spatial positions on the proximal optic array surface of the fiber optic sensor. The controller then identifies and quantifies the light emerging at each precise spatial position; and is able to mathematically calculate and correlate the light energy data with specific parameters in order to provide meaningful determinations for specific assay purposes.

V. Empirical Measurements and Data Using the Improved Fiber Optic Sensor and Detection Apparatus Using the constructed fiber optical sensor having both a photopolymerized fluorescein dye at once precise spatial position and a photopolymerized ruthenium dye at a second precise spatial position on the distal optic array surface of the optic sensor, the ability to utilize each of these dyes individually at their own specific wavelengths of light energy will be demonstrated. The photopolymerized fluorescein dye is employed for the measurement of pH in accordance with the procedure described within Munkholm et al. ]Anal. Chem. 58:1427 (1986)], the text of which is expressly incorporated position on the distal optic array surface of the sensor after reactive contact with a fluid sample; and that the emerging light from the dye sensing zone from each immobilized dye after reactive content with its own individual analyte of interest would then be recognized via its controlled emergence from only precise spatial positions which allow it to be detected and measured independently without interference in the shortest possible time period. The fully automated, computer controlled system thus allows multiple determinations, measurements and detections to be made within fractions of a second concurrently without accidental mixing or interferences between the emergent light at different spatial positions on the proximal optic array surface of the fiber optic sensor. The controller then identifies and quantifies the light emerging at each precise spatial position; and is able to mathematically calculate and correlate the light energy data with specific parameters in order to provide meaningful determinations for specific assay purposes.

V. Empirical Measurements and Data Using the Improved Fiber Optic Sensor and Detection Apparatus Using the constructed fiber optical sensor having both a photopolymerized fluorescein dye at once precise spatial position and a photopolymerized ruthenium dye at a second precise spatial position on the distal optic array surface of the optic sensor, the ability to utilize each of these dyes individually at their own specific wavelengths of light energy will be demonstrated. The photopolymerized fluorescein dye is employed for the measurement of pH in accordance with the procedure described within Munkholm et al. ]Anal. Chem. 58:1427 (1986)], the text of which is expressly incorporated by reference herein. Similarly, the photopolymerized ruthenium dye is employed for measurement of oxygen concentration in a fluid sample using the procedure described by Wolfbeis et al. ]Anal. Chem. 60:2028 (2988)], the text of which is also expressly incorporated by reference herein. This purposefully prepared fiber optic sensor able to detect and measure both pH and oxygen concurrently is employed with the apparatus previously illustrated within FIG. 22 using the fully automated computerized imaging and processing system described therein.

As regards the nature of the immobilized fluorescein and ruthenium dyes disposed at precise spatial locations on the distal optic array surface of the fiber optic sensor, the spectral properties of these dyes are recognized as fluorophores having overlapping excitation light wavelengths and moderately overlapping emission light wavelengths as indicated within Table I previously herein Alternatively, if the user wishes, one or more oxygen dyes having identical excitation light and emission light wavelengths could also be employed without difficulty due to the spatial resolution of light energy provided by the fiber optic sensor.

Experiment 1: Visualization of the Individual Immobilized Dyes

To demonstrate the ability to visualize and employ the immobilized dyes disposed precisely at individual spatial positions on the distal optic array surface of the fiber optic sensor, the emerging light energy from each of the pH and oxygen sensing dyes after introduction of exciting light was detected and processed as an image using the controlled image processing system of the automated apparatus. The images were then visualized via television monitor displays using the computerized control system. Subsequently, slight variations in excitation light wavelengths were employed in order to determine whether a better or worse visualized image could be obtained by the computer processing imaging system. The results of using slightly different wavelengths of exciting light energy conveyed specifically to a precise spatially positioned dye are provided by FIGS. 23A–23D respectively.

As shown therein, the detected emission light wavelengths from each dye individually were processed and appeared as complete images on the television monitors and revealed two distinct substantially circular immobilized dye images which correspond in location to the specific numerical coordinates for each specifically positioned dye individually. As noted by the differences in image intensity and background noise on the monitor displays, the intensity of the visualized light image varies somewhat depending on the operating conditions of the automated system. Nevertheless, each dye is clearly and distinctly visible; provides variance in emission light energy; and is identifiable and distinguishable from the other on the basis of its precise spatial positioning on the distal optic array surface of the fiber optic sensor.

Experiment 2: Contour Intensity Plots

A second experiment was conducted in accordance with the procedure described for Experiment 1 above, in which the detected and measured emission light wavelengths from each of the immobilized dyes at individual spatial positions on the distal optic array surface of the fiber optic sensor were processed as contour plots to determine the intensity as a visual display. The computerized software program permits such graphic displays to be visualized on a television monitor using the emission light from each dye after excitation. Accordingly, exciting light energy was introduced to the proximal optic array surface and then conveyed by fiber optical strands within the fiber optical sensor to each of the immobilized dyes individually on the distal optic array surface; and the emitted light conveyed to the proximal optic array surface in return was detected and measured using the computerized imaging processing automated system. The results are visualized and displayed on a monitor as shown by FIGS. 24A and 24B respectively.

Figure 24A:
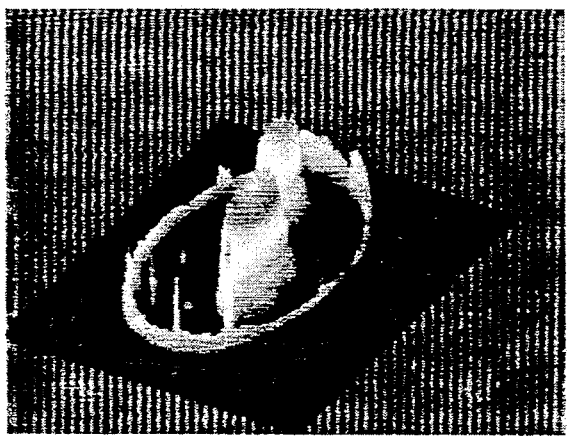
FIGS. 24A and 24B are imaging photographs of contour plots of light intensity for the individual dye deposits of FIG. 14 using the apparatus of FIG. 23.
Figure 24B:
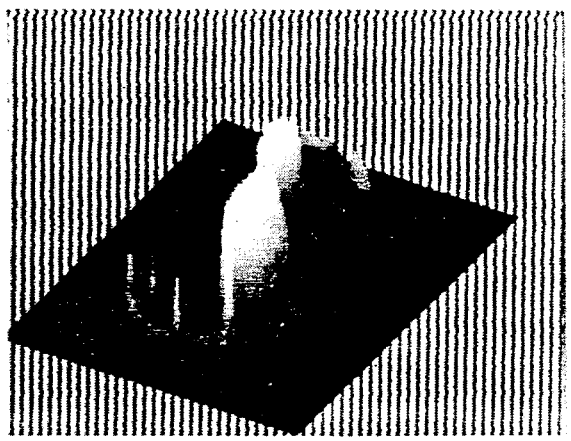

A close inspection of FIG. 24A in particular shows the location of each photopolymerized dye at an individual spatial position on the distal surface; and shows each disposed dye to be involved in the discharge of the emitted light. FIG. 24B also shows each photopolymerized dye individually to be involved during the absorbance of exciting light wavelengths and the subsequent discharge of emitting light wavelengths. These contour plots of light intensity reveal that the photopolymerized dyes themselves maintain their positional and spatial integrity during use; and are able to display their own characteristic light absorbing and light emitting properties by being held in adjacent position at precise locations on the distal optic surface of the fiber optic sensor.

Experiment 3: Empirical Measurement of pH Values

Figure 25A:
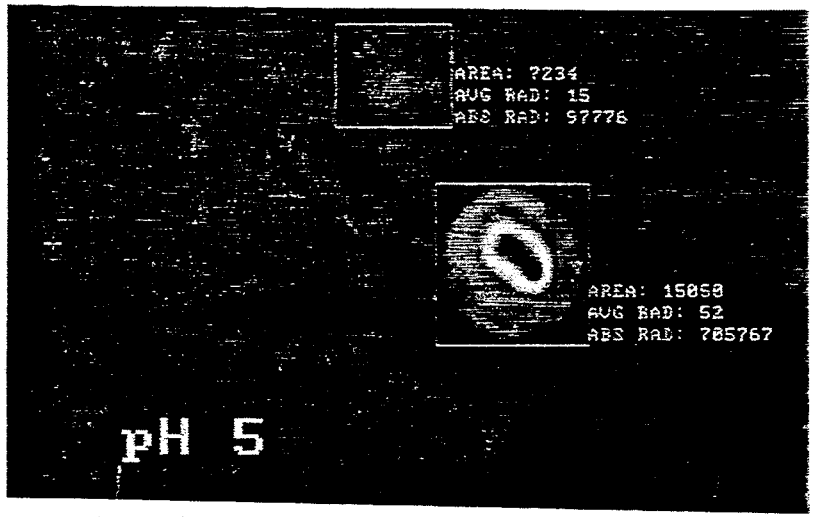
FIGS. 25A–25C, are imaging photographs and data displays provided by one dye deposit of FIG. 14 to measure pH values using the apparatus of FIG. 23.
Figure 25B:
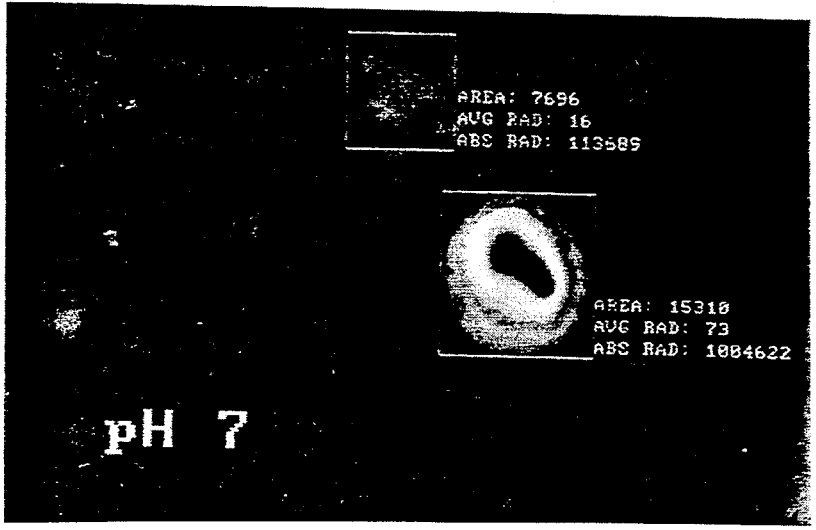
Figure 25C:
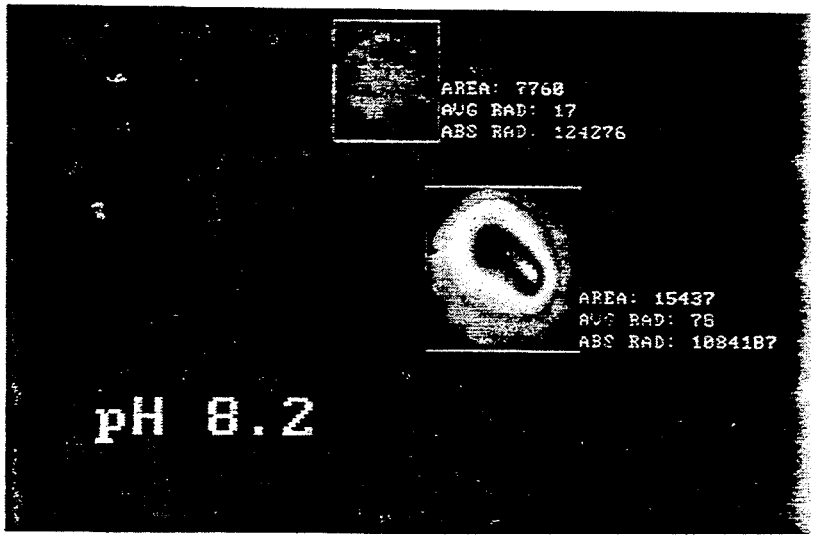

The fiber optic sensor was prepared as previously described and placed in a sample holder and subjected to reactive contact with different fluid samples in series, each fluid sample being specifically formulated at a different pH value. The individual pH values for each fluid sample were: pH 5; pH 7; and pH 8.2 respectively. Each fluid sample was individually introduced and allowed to make reactive contact with the distal optical array surface of the constructed fiber optical sensor evaluated previously in Experiments 1 and 2. For measurement and detection purposes, only a single exciting light energy maintained at a wavelength of 488 nm was introduced to the entire proximal optic array surface and conveyed to both photopolymerized dyes disposed on the distal optic array surface. After the exciting light energy was received at the distal surface, the subsequent light energy was received at the distal surface, the subsequent emissions of light energy returning from the dye after reactive contact with each individual fluid sample were detected, measured, and visualized on the monitors using the computerized imaging systems. The individual values and displays observed for each of the fluid samples having different pH values are shown by FIGS. 25A, 25B and 25C individually.

It will be noted and appreciated that the computerized imaging and processing system also allows the important technical data and correlations to be displayed on the monitor as well as the display of a discrete image of the illuminated photopolymerized fluorescein dye as it reacts with the fluid samples individually. Thus, the image obtained with the fluid sample known to be pH 5 is measured and calculated to have a precise radiation value. Note also that the visual display provides information regarding the total area involved, the average radiation, and the absolute radiation in each instance. Thus, as noted by the empirical data displayed by FIG. 25, the detected and visualized raw data can be directly correlated and standardized to give precise pH values and determinations with any unknown fluid sample—using the data of FIG. 25 as a test standard.

It will be appreciated via FIG. 25 that the visual image displayed upon the monitor shows the presence of both dyes illuminated with a single wavelength. Even though there is moderate overlap of the dyes' emission spectrum, both dyes are discernable completely due to the spatial resolution. Nevertheless, because the exciting light used in the photopolymerization was introduced in precise locations identifiable from specific numerical coordinates; and the only fluorescence comes from these location coordinates, there is no doubt that, the fluorescence detected comes from only that dye containing polymer at that photopolymerized numerical coordinate Experiment 4: A pH Sensor Having Three Distinct Depositions of A Single Dye Reagent A pH sensing fiber optical sensor was constructed employing the imaging fiber optic array in which three distinct and discernible cones of a single dye reagent were immobilized on the distal optic array surface using the photopolymerization methodology previously described herein. The pH sensing dye admixture was prepared as follows: to a 4.0 ml glass vial was added 1.0 ml of polymer stock solution (7.95 M 2-hydroxyethyl methacrylate in n-propanol), 1.0 ml of stock methylene bisacrylamide solution (0.078 M methylene bisacrylamide in n-propanol), 1.0 ml of pH 5.4 phosphate buffer, 3.0 mg acryloyl fluorescein in 0.5 mls of n-propanol, and 100 mg benzoin ethyl ether in 1 ml n-propanol. The solution was deoxygenated with molecular nitrogen for 20 minutes.

By immersing the distal optic array surface into this pH dye admixture and introducing light energy to different portions of the other proximal optic array surface in succession, three distinct and individually discernible depositions of the one dye reagent at precisely known spatial positions on the immersed optic array surface. The fully constructed three cone sensor is illustrated by FIGS. 26A and 26B.

Figure 26A:
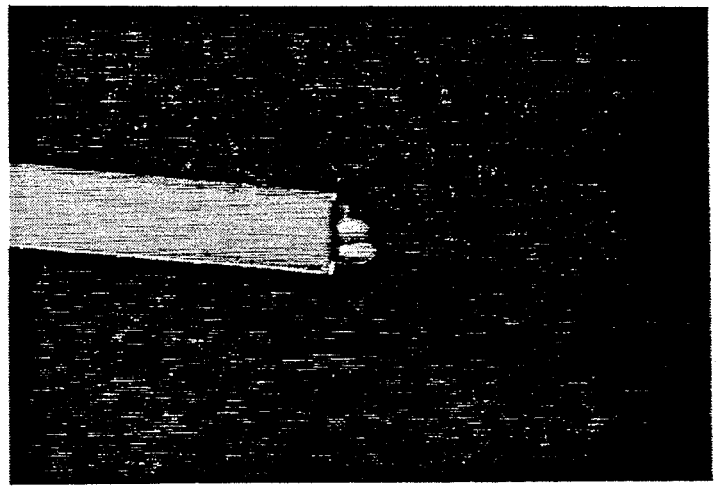
FIGS. 26A and 26B are photographic and schematic illustrations of a fiber optic sensor having three discrete pH sensitive depositions of dye reagent for sensing pH.
Figure 26B:
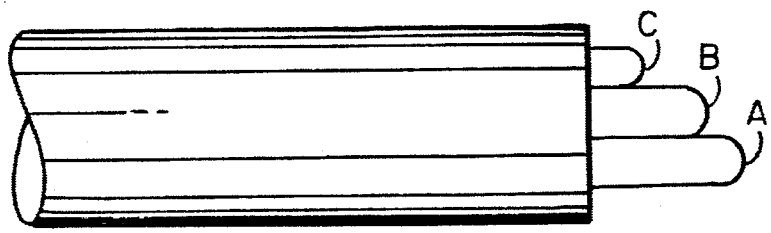

FIG. 26A shows the side-view photograph taken under a light microscope of the constructed pH sensor that has three discrete pH sensitive polymer cones protruding from its distal face FIG. 26B is a schematic drawing identifying the cones individually. The sensor body is 300 microns in diameter. The approximate dimensions of the polymer cones (diameter by height): cone A, 125 um by 140 um; cone B, 125 um by 123 um; and cone C, 125 um by 70 um.

Figure 27A:
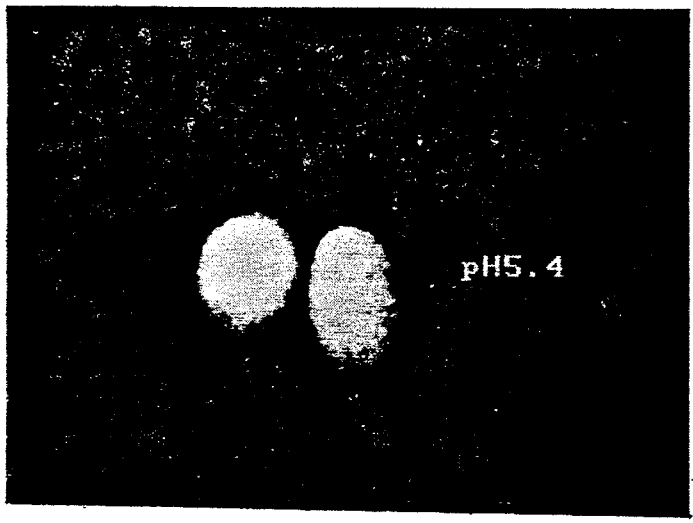
FIGS. 27A–27C illustrate the fluorescence intensity of the pH sensor of FIG. 26.
Figure 27B:
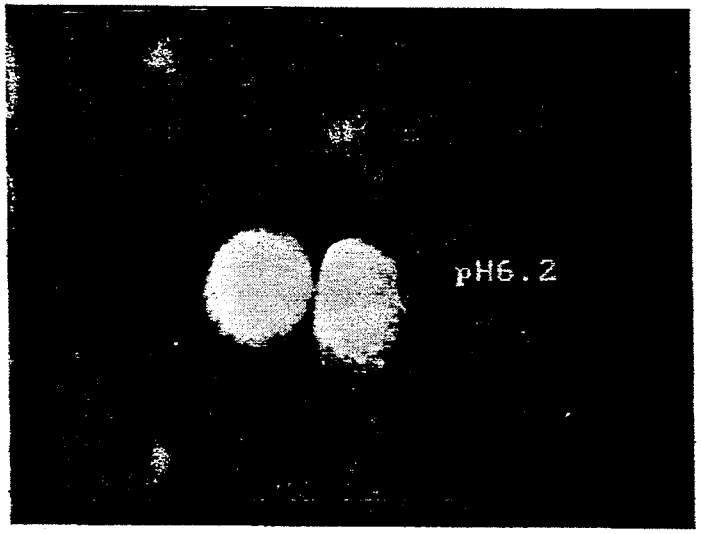
Figure 27C:
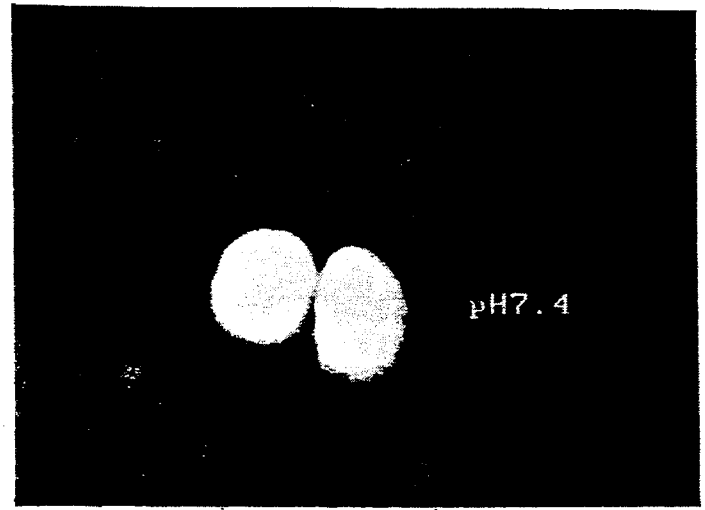

The pH sensor was tested by submerging in phosphate buffer solutions of different pH value and capturing the emitted fluorescence image with the automated apparatus using a camera. FIGS. 27A, 27B and 27C show the fluorescence intensities detected at the sensor's proximal optic surface, which is the transmitted image of the distal optic surface, containing the three individual pH-sensitive cones in pH 5.4, 6.2, 7.4, respectively. The polymer cones appear as distinctly separate fluorescent oval spots. The spots appear oval because the optic surface of the sensor was not aligned perfectly perpendicular to the camera. In pH 5.4 (FIG. 27A), cone A is not visible and cones B and C appear as coarsely-grained off-white spots. However, in pH 7.4 (FIG. 27C), all three cones' intensities increased: cone A is visible and appears as a coarsely-grained grey spot, whereas cones B and C appear as solid opaque white spots. The increase in intensity demonstrates the pH sensitivity of the cones and is consistent with the spectral properties of fluorescein.

Figure 28A:
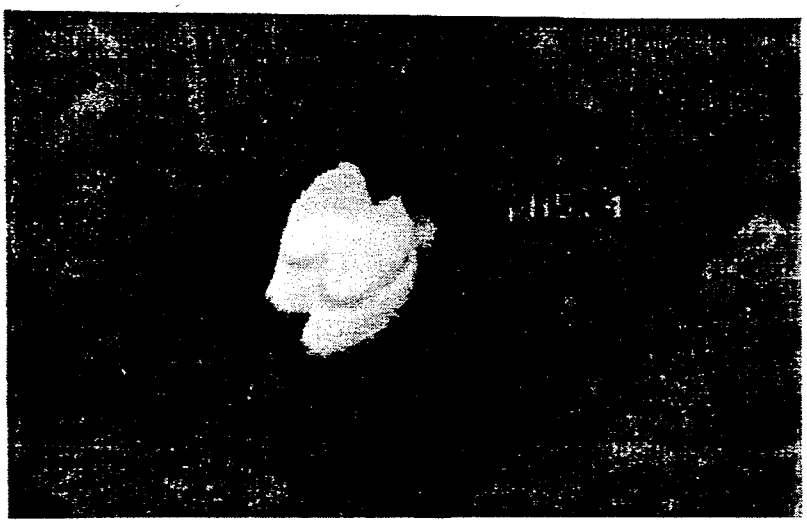
FIGS. 28A–28C illustrate a computer generated three-dimensional analysis of the fluorescence intensity of FIG. 27.
Figure 28B:
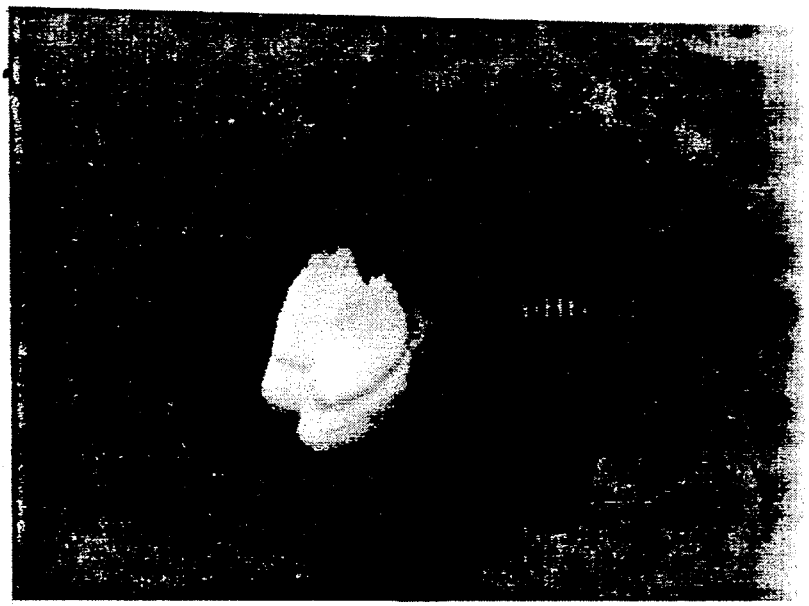
Figure 28C:
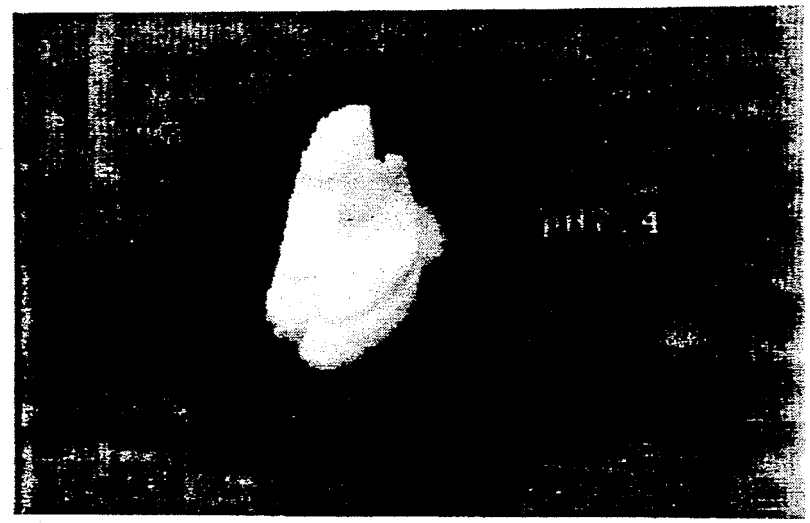

To view clearly the change in intensity of these areas, a computer generated three-dimensional analysis (x and z axes coordinate spatial position and y axis represents intensity) of the respective images was plotted as is shown by FIGS. 28A, 28B and 28C. The response of the sensor with changes in pH can be seen via the increase in intensity (y-dimension) of the cones with increasing pH. In addition, color was computer-assigned to the different grey levels the camera detects—the greater the light intensity, the brighter the color (white representing saturation of the CCD). Therefore, pH sensitivity can also be represented by a color change of each cone for the three pHs investigated.

Experiment 5: An Improved pH and Oxygen Concentration Sensor

An improved multiparameter fiber optic sensor was constructed with both pH and pO2 sensitive dye cones polymerized on its distal optic array surface. The two dye reagent admixture solutions used to make this dual parameter sensor are described below.

The pH sensing dye admixture was prepared as follows. An aqueous solution of 5.67 M acrylamide was prepared in phosphate buffer (pH 6.6). A solution of 0.0726 M methylene bisacrylamide was prepared in n-propanol. A typical stock solution comprised of 5 mls of acrylamide, 5 mls of bisacrylamide, 3.0 mgs of acryloyl fluorescein, preferably prepared in a glass container. The stock solution was then deoxygenated by bubbling molecular nitrogen into the prepared mixture for 20 minutes. In addition, a photoinitiator solution of 100 mgs of benzoin ethyl ether in 1 ml of n-propanol is freshly prepared. The final admixture is made by combining 1 ml of stock solution and 1 ml of the photoinitiator solution.

The oxygen sensing dye admixture was prepared as follows. A stock solution was made by dissolving 20 mls of methylacryloxypropl T-structure polydimethylsiloxane polymer [Petrarch Systems, Bristol Pa. in 20 mls of methylene chloride. An admixture was made by adding 100 mgs of tris (2,2'-bipyridyl ruthenium (II) chloride hexahydrate [Aldrich Company, Milwaukee, Wisc.] in 2 mls of n-propanol to 10 mls of the polymer solution. This admixture was then deoxygenated by bubbling molecular nitrogen in the solution for 15 minutes In addition, a photoinitiator solution of 100 mgs of benzoin ethyl either in 1 ml of methylene chloride is freshly prepared. The final admixture was prepared by adding 1 ml of the polymer/dye solution and 1 ml of the photoinitiator solution to a glass vial. The admixtures were then photopolymerized as dye deposits following the process previously described herein.

Figure 29A:
FIGS. 29A and 29B illustrate the capacity of a dual pH and $O_2$ sensor to detect oxygen in a sample.
Figure 29B:

This dual pH and $O_2$ sensor was tested by submerging it in a pH 7.6 phosphate buffer solution saturated with molecular oxygen (FIG. 29A); or in a pH 7.6 phosphate buffer solution which has been deoxygenated (FIG. 29B). Note that FIGS. 29A and 29B are video images of the distal face of the duel sensor. The smaller spot is the oxygen sensitive image and the large white spot is the pH sensitive image. The video image has been computer-processed to assign colors to the different intensity levels recorded by the camera. The images of FIGS. 29A and 29B show the response of the sensor to the oxygen saturated and deoxygenated buffers. Notice that the oxygen sensitive spot increases its intensity in the low oxygen buffer. This is consistent with the spectral properties of the ruthenium dye containing polymer. As the oxygen sensitive spot is exposed to higher concentrations of oxygen its fluorescence intensity decreases. It should be appreciated that as the concentration of oxygen changes, the fluorescence intensity of the pH-sensitive spot does not change.

Experiment 6: An Improved Sensor For
Detection of pH and Carbon Dioxide Concentration A multiparameter sensor was constructed that has both pH and pCO2 sensitive dye reagent cones polymerized on its distal face. The pH sensing dye cone was fabricated and deposited using the solution described in Experiment 5 previously. The $p^{CO_2}$ dye sensing cone was prepared as follows:

The $CO_2$ sensing dye reagent is constructed of two regions a pH sensing layer and a gas permeable layer. First, a polymer island is laid done on the distal surface of the imaging fiber optic array using the same procedure as for depositing the pH dye, except the polymerization is monitored and stopped when the polymer island is still small, approximately 20 microns in height as appears from a sideview. The distal surface is then soaked in 0.05 M bicarbonate buffer. Second, a stock polymer solution is prepared by dissolving 5 mls of methylacryloxypropyl T-structure polydimethylsiloxane polymer [Petrarch Systems, Bristol, Pa.] in 5 mls of methylene chloride. In addition, a photoinitiator solution of 100 mgs of benzoin ethyl ether in 1 ml of methylene chloride is freshly prepared. The final dye admixture is prepared by adding 1 ml of the photoinitiator solution and 1 ml of the stock polymer solution to a glass vial. The small pH spot is then illuminated again to cause it to become coated with a silicone polymer layer—thereby rendering the deposit sensitive to $CO_2$ and insensitive to pH.

Figure 30:
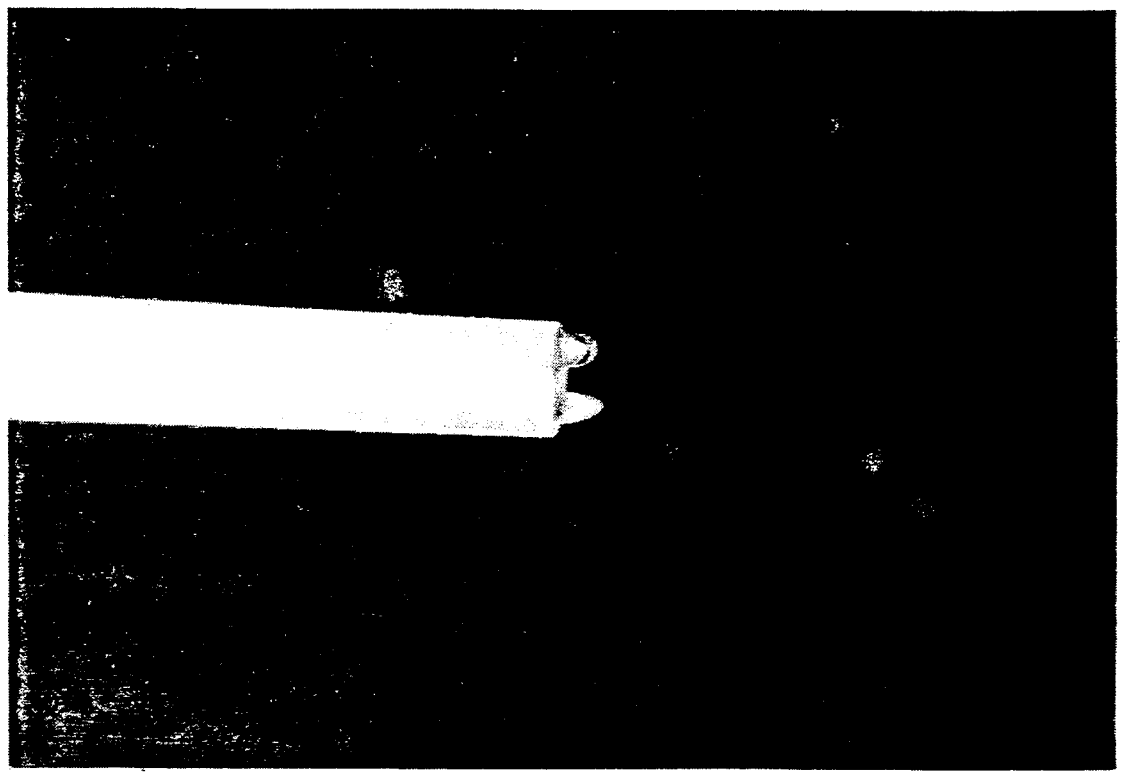
FIG. 30 is a photograph illustrating the construction of a $pCO_2$ sensing dye in a dual pH and $pCO_2$ sensor.

FIG. 30 shows the distal optic array surface of the fully constructed pH and $p^{CO_2}$ sensor as a side-view photographed under a light microscope. Clearly, FIG. 30 reveals that the $p^{CO_2}$ dye cone is composed of two layers: a pH sensitive layer and a gas-permeable membrane. The pH layer appears as a small white cone, whereas, the gas-permeable membrane is like a white halo covering the pH layer.

The present invention is not to be restricted in form nor limited in scope except by the claims appended hereto.

What we claim is:

1. A fiber optic sensor useful in an apparatus for detecting at least one analyte of interest in a fluid sample, the detection of each analyte being correlatable with an individual optical determination, said fiber optic sensor comprising:

a preformed, unitary fiber optic array comprising a plurality of individually clad, fiber optic strands disposed co-axially along their lengths and having two discrete optic array ends each of which is formed of multiple strand end faces, said preformed, unitary fiber optic array being of determinable configuration and dimensions, said two discrete optic array ends of said preformed, unitary fiber optic array presenting two discrete optic array surfaces for introduction and conveyance of light energy;

at least one sensing zone comprising not less than one light energy absorbing dye disposed as an uninterrupted deposit in aligned organization upon multiple strand end faces on one of said discrete optic fiber array surfaces of said preformed, unitary fiber optic array, the different spatial positioning of each uninterrupted dye deposit in aligned organization within said at least one sensing zone on said one of said discrete surfaces serving to identify and distinguish each light energy absorbing dye from all other light energy absorbing dyes disposed within said at least one sensing zone, each spatially positioned uninterrupted dye deposit reacting with one analyte of interest; and at least one sample viewing zone adjacent to said at least one sensing zone on said one of said discrete optic array surfaces of said preformed, unitary fiber optic array, said at least one sample viewing zone being formed of said multiple strand end faces in aligned organization and in fixed spatial position on said discrete optic array surface.

2. The fiber optic sensor as recited in claim 1 wherein said sensing zone comprises at least two different light energy absorbing dyes disposed individually at different spatial positions on said one of said discrete optic array surfaces.

3. The fiber optic sensor as recited in claim 1 wherein the wavelength of light energy absorbed by said not less than one light energy absorbing dye is selected from the group consisting of infrared, visible and ultraviolet wavelengths.

4. The fiber optic sensor as recited in claim 1 wherein said not less than one light energy absorbing dye is selected from the group consisting of fluorophores, fluorescent enzyme substrates, and fluorescent antibody conjugates.

5. An apparatus for detecting at least one analyte of interest in a fluid sample, the detection of each analyte being correlatable with an individual optical determination, said apparatus comprising:

a fiber optic sensor comprised of
(a) a preformed, unitary fiber optic array comprising a plurality of individually clad, fiber optic strands disposed co-axially along their lengths and having two discrete optic array ends each of which is formed of multiple strand end faces, said preformed, unitary fiber optic array being of determinable configuration and dimensions, said two discrete optic array ends of said preformed, unitary fiber optic array presenting two discrete optic array surfaces for introduction and conveyance of light energy;
(b) at least one sensing zone comprising not less than one light energy absorbing dye disposed as an uninterrupted deposit in aligned organization upon said multiple strand end faces at different spatial positions on one of said discrete optic fiber array surfaces of said preformed, unitary fiber optic array, the different spatial positioning of each uninterrupted dye deposit in aligned organization within said at least one sensing zone on said one of said discrete surfaces serving to identify and distinguish each light energy absorbing dye from all other light energy absorbing dyes disposed within said at least one sensing zone, each spatially positioned uninterrupted dye deposit reacting with one analyte of interest; and
(c) at least one sample viewing zone adjacent to said at least one sensing zone on said one of said discrete optic array surfaces of said preformed, unitary fiber optic array, said at least one sample viewing zone being formed of said multiple strand end faces in aligned organization and in fixed spatial position on said one of said discrete optic array surface ends;

means for placing said spatially positioned uninterrupted dye deposit within said at least one sensing zone on one of said discrete optic array surfaces of said fiber optic sensor into reactive contact with a fluid sample;

means for introducing light energy to one of said discrete optic array surfaces of said fiber optic sensor such that said plurality of individually clad fiber optical strands convey said introduced light energy concurrently and illuminate said spatially positioned uninterrupted dye deposit within said at least one sensing zone on said optic array surface;

means for detecting emerging light energy from said illuminated spatially positioned uninterrupted dye deposit within said at least one sensing zone on one of said discrete optic array surfaces, said detected emerging light energy serving as an optical determination for one analyte of interest in the fluid sample; and means for concurrently observing the fluid sample via said at least one sample viewing zone on one of said discrete optic array surfaces.

6. The detection apparatus as recited in claim 5 further comprising automated means for concurrently introducing light energy and detecting emerging light.

7. The detection apparatus as recited in claim 5 wherein said means for detecting emerging light energy provides a visualized discrete optical image.

8. The detection apparatus as recited in claim 5 further comprising a computer controlled imaging and data processing system.

9. A method for detecting at least one analyte of interest in a fluid sample, the detection of each analyte being correlatable with an individual optical determination, said method comprising the steps of:

obtaining a fiber optic sensor comprised of
(a) a preformed, unitary fiber optic array comprising a plurality of individually clad, fiber optic strands disposed co-axially along their lengths and having two discrete optic array ends each of which is formed of multiple strand end faces, said preformed, unitary fiber optic array being of determinable configuration and dimensions, said two discrete optic array ends of said preformed, unitary fiber optic array presenting two discrete optic array surfaces for introduction and conveyance of light energy;
(b) at least one sensing zone comprising not less than one light energy absorbing dye disposed as an uninterrupted deposit in aligned organization upon said multiple strand end faces at different spatial positions on one of said discrete optic fiber array surfaces of said preformed, unitary fiber optic array, the different spatial positioning of each uninterrupted dye deposit in aligned organization upon said one of said discrete optic array surfaces serving to identify and distinguish each light energy absorbing dye from all other light energy absorbing dyes disposed within said at least one sensing zone, each spatially positioned uninterrupted dye deposit reacting with one analyte of interest; and
(c) at least one sample viewing zone adjacent to said at least one sensing zone on said one of said discrete optic array surfaces of said preformed, unitary fiber optic array, said at least one sample viewing zone being formed of said multiple strand end faces in aligned organization and in fixed spatial position on said one of said discrete optic array surfaces;

placing said spatially positioned uninterrupted dye deposit within said at least one sensing zone on one of said discrete optic array surfaces of said fiber optic sensor into reactive contact with a fluid sample;

introducing light energy to one of said discrete optic array surfaces of said fiber optic sensor such that said plurality of individually clad fiber optical strands convey said introduced light energy concurrently and illuminate said spatially positioned uninterrupted dye deposit within said at least one sensing zone on said optic array surface;

detecting emerging light energy from said illuminated spatially positioned uninterrupted dye deposit within said at least one sensing zone on one of said discrete optic array surfaces, said detected emerging light energy serving as an optical determination for one analyte of interest in the fluid sample; and concurrently observing the fluid sample via said at least one sample viewing zone on one of said discrete optic array surfaces.

10. The detection method as recited in claim 9 wherein said detection is made in-vivo.

11. The detection method as recited in claim 9 wherein said detection is made in-vitro.

12. The detection method as recited in claim 9 wherein said detection is made using an automatic imaging and data processing system.

* * * * *